(12) United States Patent
Gharib et al.

(10) Patent No.: US 10,517,911 B2
(45) Date of Patent: Dec. 31, 2019

(54) MANUFACTURING METHODS, COMPOSITIONS, AND MEDICAL APPLICATIONS OF ORALLY ADMINISTERED CANNABIS PHARMACEUTICALS USING REPRESENTATIVE/TOTAL/COMPLETE CANNABIS EXTRACTIONS (CANNABIS INFUSED PILLS)

(71) Applicant: HARVEST DIRECT ENTERPRISES LLC, Everett, WA (US)

(72) Inventors: Zeyead Gharib, Everett, WA (US); Ahmed Gharib, Everett, WA (US)

(73) Assignee: Harvest Direct Enterprises LLC, Everett, WA (US)

( * ) Notice: Subject to any disclaimer, the term of this patent is extended or adjusted under 35 U.S.C. 154(b) by 14 days.

(21) Appl. No.: 15/588,505

(22) Filed: May 5, 2017

(65) Prior Publication Data
US 2017/0333505 A1    Nov. 23, 2017

Related U.S. Application Data

(60) Provisional application No. 62/332,513, filed on May 6, 2016, provisional application No. 62/467,060, filed on Mar. 3, 2017.

(51) Int. Cl.
| | |
|---|---|
| *A61K 36/00* | (2006.01) |
| *A61K 36/185* | (2006.01) |
| *A23L 29/00* | (2016.01) |
| *A61K 9/00* | (2006.01) |
| *A61K 9/48* | (2006.01) |
| *A61K 31/01* | (2006.01) |
| *A61K 31/015* | (2006.01) |
| *A61K 31/045* | (2006.01) |
| *A61K 31/05* | (2006.01) |
| *A61K 31/192* | (2006.01) |
| *A61K 31/352* | (2006.01) |
| *B01D 11/02* | (2006.01) |

(52) U.S. Cl.
CPC ............ *A61K 36/185* (2013.01); *A23L 29/03* (2016.08); *A61K 9/0053* (2013.01); *A61K 9/48* (2013.01); *A61K 31/01* (2013.01); *A61K 31/015* (2013.01); *A61K 31/045* (2013.01); *A61K 31/05* (2013.01); *A61K 31/192* (2013.01); *A61K 31/352* (2013.01); *B01D 11/0257* (2013.01); *A23V 2002/00* (2013.01); *A61K 2236/17* (2013.01); *A61K 2236/33* (2013.01); *A61K 2236/331* (2013.01); *A61K 2236/35* (2013.01); *A61K 2236/37* (2013.01); *A61K 2236/53* (2013.01)

(58) Field of Classification Search
CPC ....................................................... A61K 36/00
USPC ........................................................... 424/725
See application file for complete search history.

(56) References Cited

U.S. PATENT DOCUMENTS

| | | |
|---|---|---|
| 5,104,539 A | 4/1992 | Anderson et al. |
| 2001/0020599 A1 | 9/2001 | Lautenschlager |
| 2004/0147767 A1 | 7/2004 | Whittle et al. |
| 2014/0296549 A1 | 10/2014 | Boam et al. |
| 2015/0080265 A1 | 3/2015 | Elzinga et al. |
| 2015/0196158 A1 | 7/2015 | Valasquez |
| 2015/0297653 A1 | 10/2015 | Speier |
| 2016/0000843 A1 | 1/2016 | Lowe et al. |
| 2016/0243178 A1* | 8/2016 | Stodola ................ A61K 31/352 |

OTHER PUBLICATIONS

Elsohly et al., Chemical constituents of marijuana: The complex mixture of natural cannabinoids, Life Sciences, vol. 78, Issue 5, pp. 539-548, 2005.
International Search Report and Written Opinion dated Aug. 25, 2017 in PCT International Application No. PCT/US2017/031404, 21 pages.

* cited by examiner

*Primary Examiner* — Michael V Meller
(74) *Attorney, Agent, or Firm* — Knobbe, Martens, Olson & Bear, LLP

(57) ABSTRACT

Disclosed herein are embodiments of cannabis extraction methods, apparatuses for extracting cannabis, and methods of using cannabis extracts.

19 Claims, 16 Drawing Sheets

Cannabinoid Profile

| Customer: |
|---|
| Strain name: THCaps by NorthWest Cannabis Solutions |

| SHL ID: 20170125-04-01 | Sample type: Oil | Submitted: 01/25/2017 |
|---|---|---|
| WSLCB Lot ID: | Sample mass: 0.9559 g | tested: 01/26/2017 |
| Test Site: SHL Washington | Instrument: HPLC-DAD | reported: 01/30/2017 |

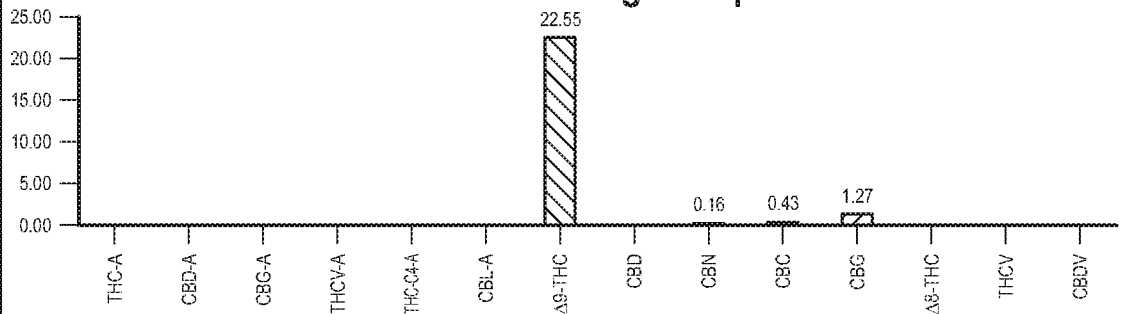

Cannabinoids as Milligrams per Milliliter

| Cannabinoid | mg/mL | mg/tsp |
|---|---|---|
| THC-A | --- | --- |
| CBD-A | --- | --- |
| CBG-A | --- | --- |
| THCV-A | --- | --- |
| THC-C4-A | --- | --- |
| CBL-A | --- | --- |
| Δ9-THC | 22.55 | 112.73 |
| CBD | --- | --- |
| CBN | 0.16 | 0.79 |
| CBC | 0.43 | 2.17 |
| CBG | 1.27 | 6.37 |
| Δ8-THC | --- | --- |
| THCV | --- | --- |
| CBDV | --- | --- |

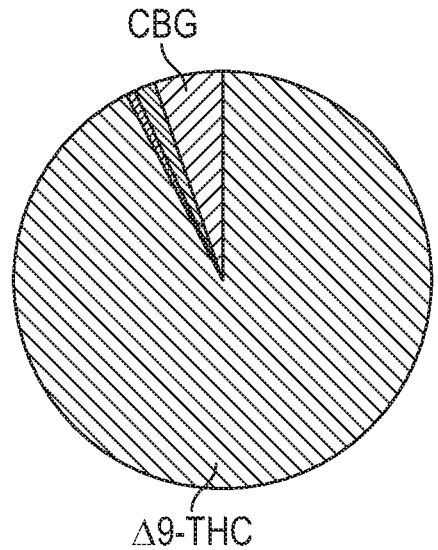

Fractions of Measured Cannabinoids

Δ9-THC Potency = [Δ9-THC] + [THC-A] x 0.877 = 22.55 + 0.00 x 0.877 = 22.55 mg/mL     density
CBD Potency = [CBD] + [CBD-A] x 0.877 = 0.00 + 0.00 x 0.877 = 0.00 mg/mL     0.96 g/mL

FIG. 19

Cannabinoid Profile

Customer:
Strain name: Weed Pillz by Harvest Direct Enterprises LLC

| | | |
|---|---|---|
| SHL ID: 20170125-04-03 | Sample type: Oil | Submitted: 01/25/2017 |
| WSLCB Lot ID: | Sample mass: 0.94 g | tested: 01/26/2017 |
| Test Site: SHL Washington | Instrument: HPLC-DAD | reported: 01/30/2017 |

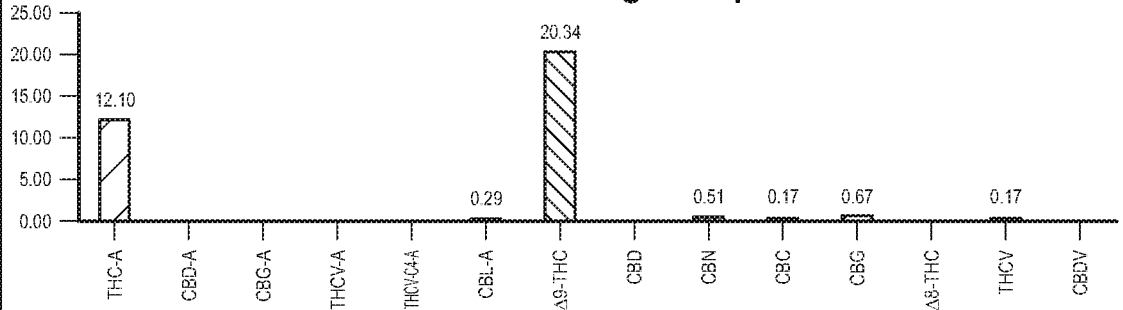

Cannabinoids as Milligrams per Milliliter

| Cannabinoid | mg/mL | mg/tsp |
|---|---|---|
| THC-A | 12.10 | 60.50 |
| CBD-A | --- | --- |
| CBG-A | --- | --- |
| THCV-A | --- | --- |
| THC-C4-A | --- | --- |
| CBL-A | 0.29 | 1.43 |
| $\Delta^9$-THC | 20.34 | 101.68 |
| CBD | --- | --- |
| CBN | 0.51 | 2.56 |
| CBC | 0.17 | 0.86 |
| CBG | 0.67 | 3.33 |
| $\Delta^8$-THC | --- | --- |
| THCV | 0.17 | 0.83 |
| CBDV | --- | --- |

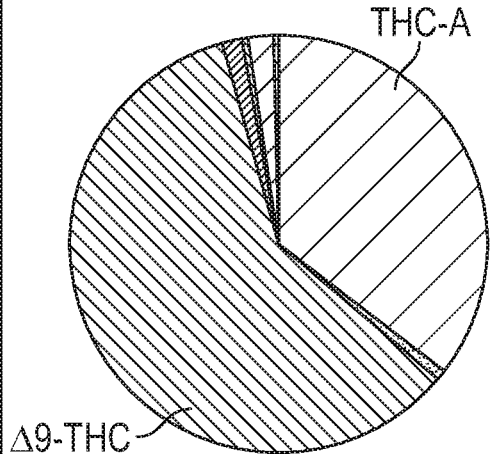

Fractions of Measured Cannabinoids $\Delta$9-THC Potency = [$\Delta$9-THC] + [THC-A] x 0.877 = 20.34 + 12.10 x 0.877 = 30.95 mg/mL
CBD Potency = [CBD] + [CBD-A] x 0.877 = 0.00 + 0.00 x 0.877 = 0.00 mg/mL density 0.94 g/mL

FIG. 21

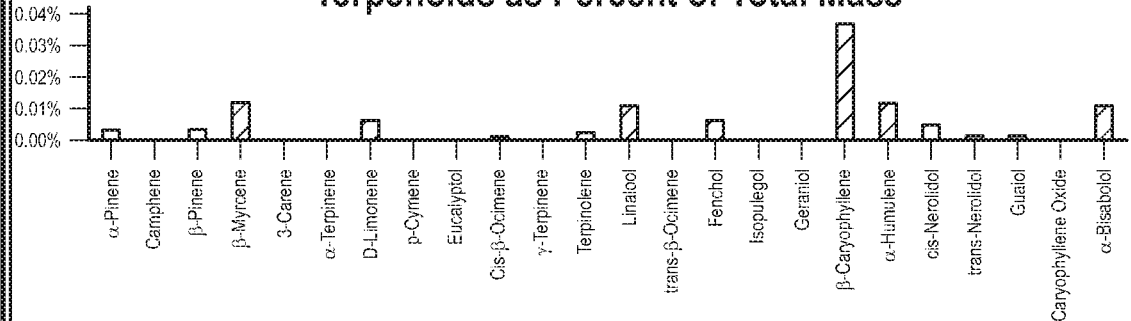
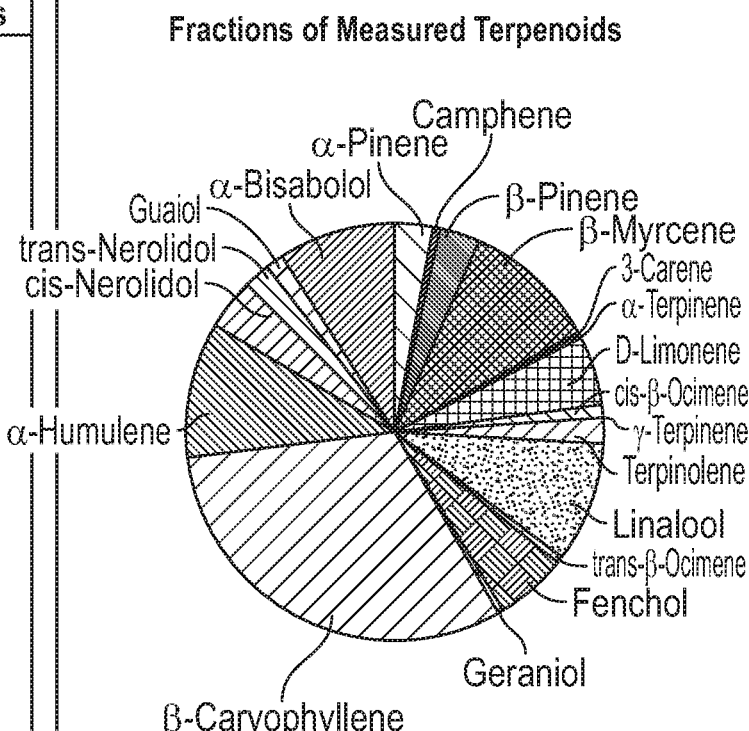
FIG. 22

MANUFACTURING METHODS, COMPOSITIONS, AND MEDICAL APPLICATIONS OF ORALLY ADMINISTERED CANNABIS PHARMACEUTICALS USING REPRESENTATIVE/TOTAL/COMPLETE CANNABIS EXTRACTIONS (CANNABIS INFUSED PILLS)

RELATED APPLICATIONS

This application is a non-provisional application of U.S. Provisional Application Ser. No. 62/332,513 filed May 6, 2016; Ser. No. 62/467,060 filed Mar. 3, 2017, each of which is hereby incorporated by reference in their entireties.

BACKGROUND

Field

Disclosed herein are embodiments of manufacturing methods and apparatuses for producing cannabis extracts.

Description of the Related Art

Some cannabis extraction methods have been described in the art. However, cannabis extraction methods that preserve all compounds of cannabis while removing byproducts have proven difficult to develop.

SUMMARY

In some embodiments, a method of extracting cannabis is provided. The method comprises (i) adding any amount of at least one species of cannabis plant or any amount of an extract of at least one species of cannabis plant to a reaction chamber, (ii) optionally producing cannabis extracts through extracting cannabis from the amount of at least one species of cannabis plant in the chamber, (iii) removing byproducts from the reaction chamber that are produced from extracting cannabis, and (iv) retaining compounds within the chamber derived from cannabis, wherein the reaction chamber comprises a filter comprising pores that allow for removal from the reaction chamber of the byproducts from the cannabis extraction process and prevent removal from the chamber of the compounds derived from cannabis.

In some embodiments, an apparatus for extracting cannabis is provided comprising an airtight container comprising (i) an inner surface, (ii) an outer surface, (iii) a reaction chamber, and (iv) a size exclusion filter, wherein the size exclusion filter comprises pores of sufficient size to allow byproducts of an extraction process and a decarboxylation process to pass through the filter but prevents compounds derived from cannabis from passing through the filter.

In some embodiments, a cannabis extraction method is provided that uses any of the cannabis extraction apparatuses disclosed herein comprising the steps of (i) adding any amount of at least one species of cannabis plant or any amount of an extract of at least one species of cannabis plant to a reaction chamber, (ii) optionally producing cannabis extracts through extracting cannabis from the amount of at least one species of cannabis plant in the chamber, (iii) removing byproducts from the reaction chamber that are produced from extracting cannabis, and (iv) retaining compounds within the chamber derived from cannabis, wherein the reaction chamber comprises a filter comprising pores that allow for removal from the reaction chamber of the byproducts from the cannabis extraction process and prevent removal from the chamber of compounds derived from cannabis.

In some embodiments, a mixture of compounds is provided comprising at least one terpene compound derived from cannabis and at least one cannabinoid compound derived from cannabis.

In some embodiments, a mixture of compounds derived from cannabis is provided that comprises cannabinoids, nitrogenous compounds, amino acids, proteins, enzymes, glycoproteins, hydrocarbons, simple alcohols, aldehydes, ketones and acids, fatty acids, simple esters and lactones, steroids, terpenes, non-cannabinoid phenols, flavonoids, vitamins, and pigments.

In some embodiments, a method of treatment is provided comprising administering a pharmaceutically acceptable amount of any pharmaceutical composition disclosed herein to a patient in need thereof.

In some embodiments, a method of treatment is provided comprising administering any pharmaceutical composition disclosed herein to treat any one or more of the following: nausea and vomiting, wasting syndrome (AIDS), lack of appetite (exhibited in cancer and AIDs patients as well as patients suffering from anorexia nervosa), multiple sclerosis, spinal cord trauma, epilepsy, pain, arthritis (and other musculoskeletal disorders), movement disorders, glaucoma, asthma, hypertension, psychiatric disorders, Alzheimer's and dementia, general inflammation, gastrointestinal disorders.

BRIEF DESCRIPTION OF THE DRAWINGS

FIG. 19 Cannabinoid analysis of THCaps by NorthWest Cannabis Solutions—a THC only formulation like Marinol.

FIG. 21 Cannabinoid analysis of Weed Pillz by Harvest Direct Enterprises—an oral pharmaceutical preparation that is made from complete/representative/total cannabis extractions.

FIG. 22 Terpene analysis of Weed Pillz by Harvest Direct Enterprises—an oral pharmaceutical preparation that is made from complete/representative/total cannabis extractions.

DETAILED DESCRIPTION

Disclosed herein are manufacturing methods, compositions, and medical applications of representative/total/complete cannabis preparations. These representative/total/complete cannabis preparations allows for the "entourage effect"; wherein the myriad of medically viable compounds found in cannabis, such as but not limited to cannabinoids and terpenes, interact in the mammalian endocannabinoid system to produce greater medical efficacy and safety.

Figure 1:
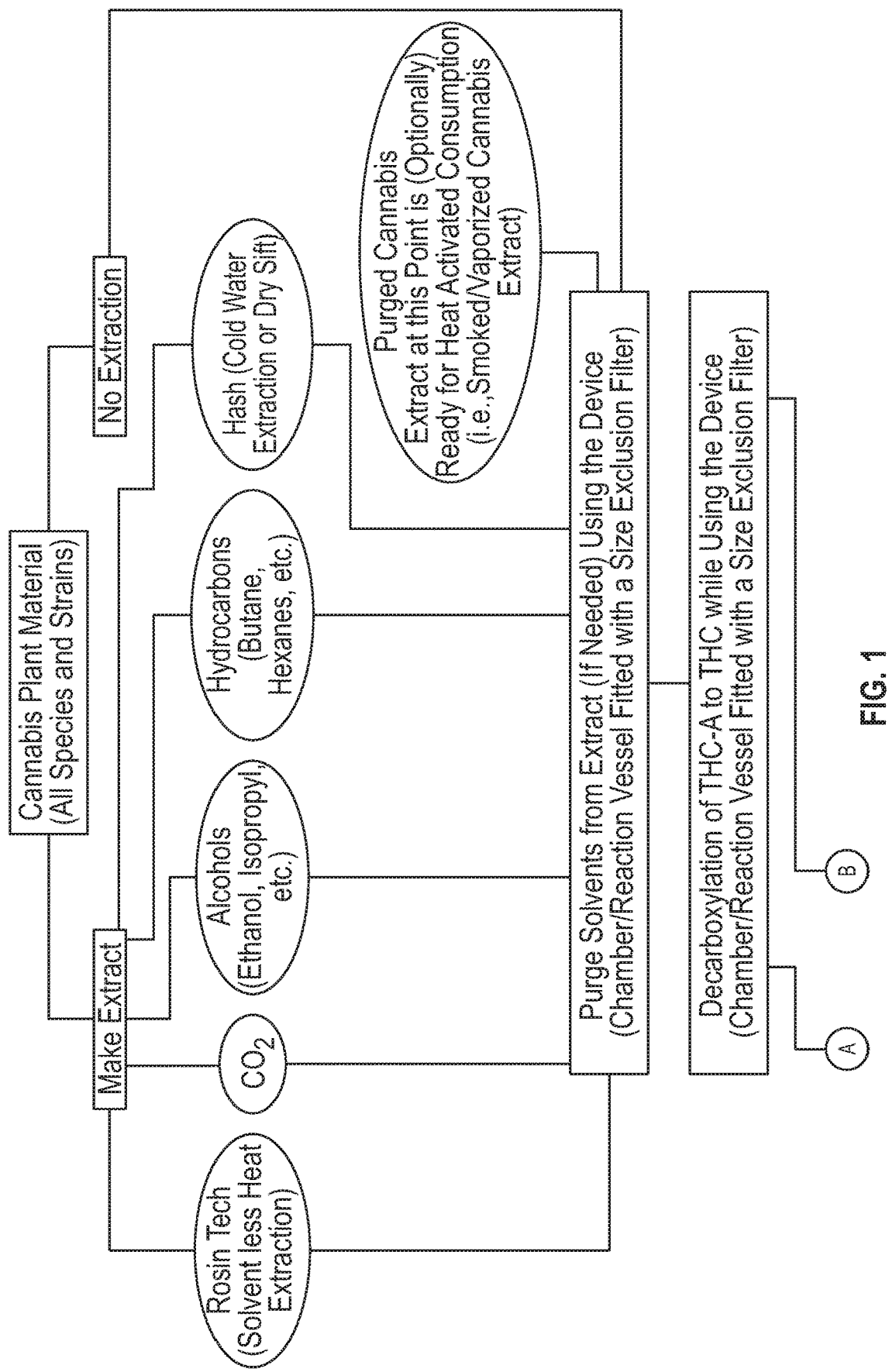
FIG. 1 depicts one embodiment of the entire process from cannabis plant material to final product (cannabis preparation).
Figure 1:
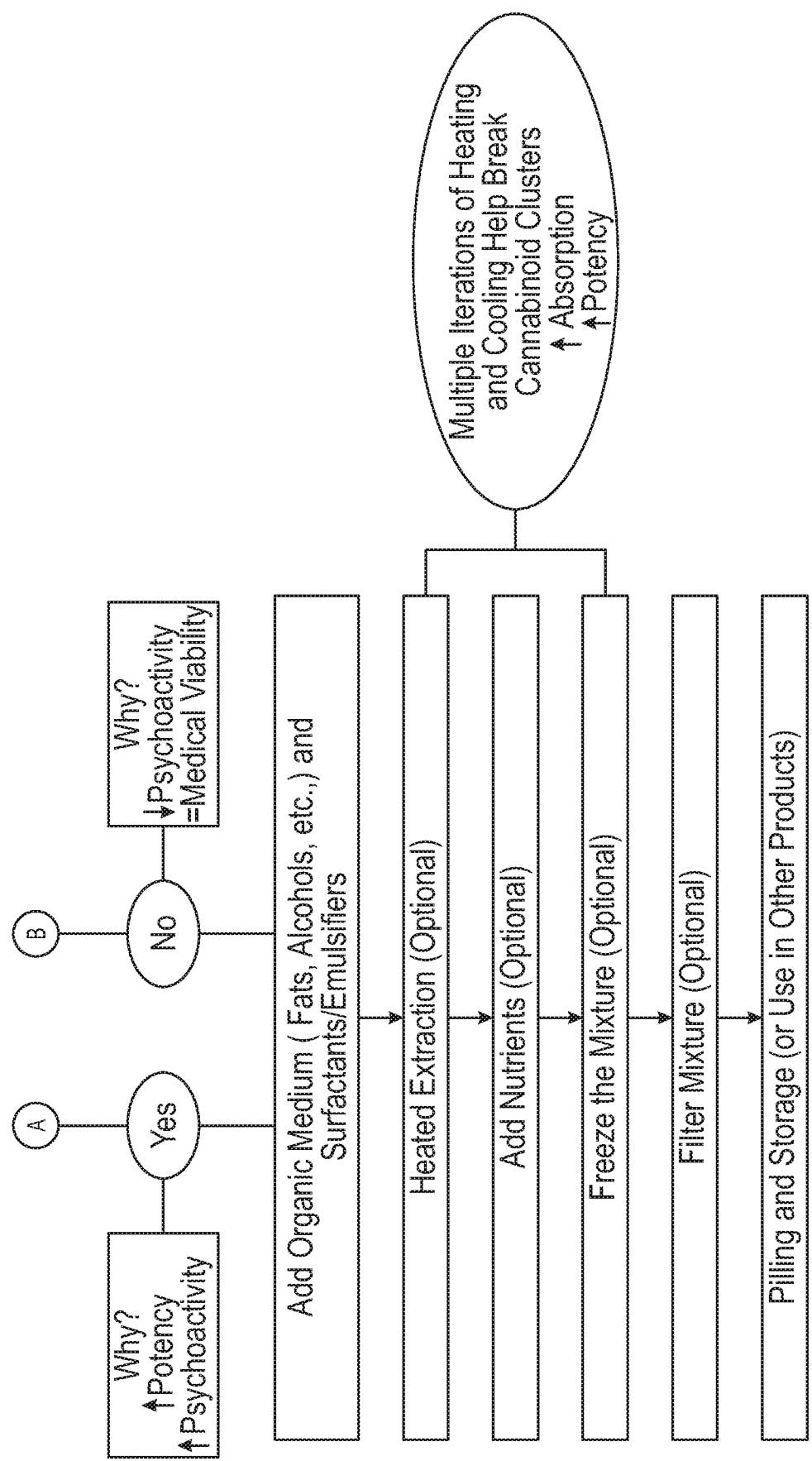
Figure 2:
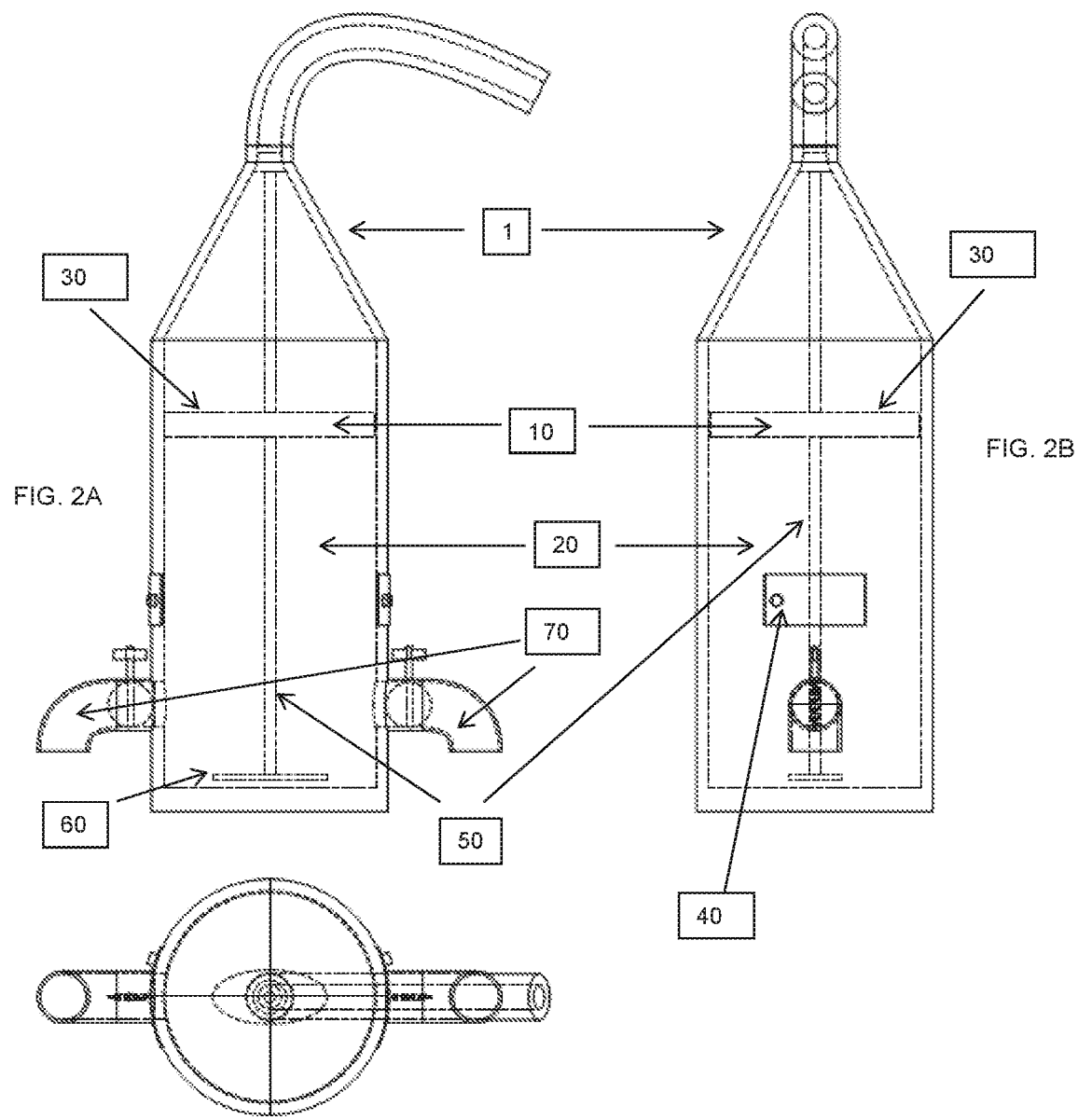
FIG. 2A depicts a front view of an embodiment of a cannabis extraction apparatus.
FIG. 2B depicts a side view of an embodiment of a cannabis extraction apparatus.
FIG. 2C depicts a top view of an embodiment of a cannabis extraction apparatus.

In some embodiments, retention of these medically viable compounds during the cannabis extract purge process and the decarboxylation process is achieved through isolating cannabis extracts through using the apparatus as depicted in FIGS. 2A, 2B and 2C. These preparations can optionally also make use of surfactants and nutrients in order to increase the bioavailability and subsequent absorption of these medically viable compounds in the mammalian gastrointestinal tract. Extractions may originate from all forms of cannabis plant material, including but not limited to *cannabis sativa, cannabis indica, cannabis ruderalis*—and any/all subspecies and any/all cross breeds thereof—in both male and female varieties.

Disclosed herein is a representative/total/complete extraction, using a variety of extraction mediums, including but not limited to: cold water extraction and dry sift (hash), $CO_2$, hydrocarbons (including but not limited to: butane, propane, hexane), alcohol (including but not limited to: ethanol, iso-propyl, methanol), and rosin tech (heat extraction)) of cannabis and any/all medically viable compounds found therein (including but not limited to cannabinoids, nitrogenous compounds, amino acids, proteins, enzymes, glycoproteins, hydrocarbons, simple alcohols, aldehydes, ketones and acids, fatty acids, simple esters and lactones, steroids, terpenes, non-cannabinoid phenols, flavonoids, vitamins, and pigments) and its species (including but not limited to *cannabis sativa, cannabis indica, cannabis ruderalis*—and any/all subspecies and any/all cross breeds thereof and any/all established strains—in both male and female varieties—using both live and dried cannabis plant material) and the subsequent conversion of these extracts into pill-able forms for oral administration (immediate and extended release) is described. In some embodiments, formulations disclosed herein will utilize the use of surfactant(s)/emulsifier(s) and nutritional compounds in order to increase the bioavailability and subsequent absorption of these orally administered cannabis pills/capsules, and the medically viable compounds found therein as a result of a total cannabis extraction, within the mammalian gastrointestinal tract (effectively bypassing the hepatic first pass effect). Varieties will include but will not be limited to: Vegan, kosher, halal, gluten free, extremely potent, CBD rich, low potency, non-decarboxylated (non-psychoactive), live plant material, allergen-free, extended release, very low or sodium free, established cannabis strains, and more.

In Marinol, only *cannabis sativa* is utilized. This oversight completely disregards the variety and distinct variations found in the *Cannabis* genus. Current research shows that the *cannabis* genus has seven sub species, including but not limited to *cannabis sativa, cannabis indica*, and *cannabis ruderalis*—any/all subspecies and any/all crossbreeds thereof and any/all established strains.

Furthermore, the prior art (Marinol) only makes use of female varieties. Current research also shows that hemp (male form of cannabis) may be particularly medicinally beneficial due to its low THC and high CBD chemotypes. This ratio is particularly interesting to medical applications due to its low psychoactivity and increased medical viability.

Furthermore, Marinol is formulated using a THC-only extract. This completely ignores the entourage effect exhibited by cannabis and other herbal remedies/formulations wherein secondary compounds increase the medical efficacy and safety of primary constituents while at the same time helping to mitigate their negative/undesirable side effects. In some embodiments, methods and compositions are disclosed herein that take advantage of the entourage effect by including as many of these medically viable compounds as possible, primarily cannabinoids and terpenes, as a result of representative/total/complete cannabis extractions. It should be noted that cannabis is comprised of at least 545 distinct compounds that span 20 chemical classes including cannabinoids, terpenes/terpenoids, amino acids, nitrogenous compounds, simple alcohols, aldehydes, ketones, esters, lactones, and acids, fatty acids, steroids, non-cannabinoid phenols, pigments, flavonoids, vitamins, proteins, enzymes, glycoproteins, and hydrocarbons. Cannabinoids and terpenes, in particular, have shown great potential in terms of medicinal value.

Also, the prior art only mentions *cannabis sativa*. The *Cannabis* genus: including *cannabis sativa, cannabis indica*, and *cannabis ruderalis* species (and the seven subspecies) and their cross breeds (including established strains) in both female and male varieties, have been shown to contain chemical compounds that have both psychotropic and medicinal effects.

*Cannabis*

The *cannabis* genus (marijuana, weed) is a wind-pollinated dioecious flowering plant that belongs to the Cannabaceae family. Current research shows that the *cannabis* genus has seven sub species, including but not limited to *cannabis sativa, cannabis indica*, and *cannabis ruderalis*—any/all subspecies and any/all crossbreeds thereof and any/all established strains. The therapeutic use of cannabis stretches back to ancient times; it was cultivated in China around 4000BC and is included in the world's oldest pharmacopoeia written by Pen Ts'ao Ching. There are three common subspecies of *cannabis: cannabis sativa* (biannual), *cannabis indica* (annual) and *cannabis ruderalis* (varies), but there are seven subspecies total. Current research shows that there are over 3,000 established cannabis strains. Growing conditions and genetics influence the characteristics of developing plants and the subsequent chemical characteristics of finished cannabis products.

Mature male plants, known as hemp, have minute cannabinoid contents and are typically used to manufacture goods and as an alternative energy source. Hemp may be medicinally beneficial due to its low THC and high CBD chemotypes, which results in low psychoactivity and increased medical viability.

The harvested flowers originating from mature female cannabis plants are characteristically higher in phytocannabinoid content and typically possess significant concentrations of other phytochemicals, such as terpenes, that are also of pharmaceutical interest. Cannabinoids and terpenes are secreted by glandular trichomes that occur most abundantly on the floral calyxes and bracts of the female marijuana plant. Dried cannabis flowers are the most basic form of cannabis. Other, more potent, preparations of cannabis include hashish (typically ranging from 20-65% tetrahydrocannabinol (THC)) and hash oil (typically ranging from 50-90% THC).

Cannabis has at least 545 distinct compounds that span 20 chemical classes including cannabinoids, terpenes/terpenoids, amino acids, nitrogenous compounds, simple alcohols, aldehydes, ketones, esters, lactones, and acids, fatty acids, steroids, non-cannabinoid phenols, pigments, flavonoids, vitamins, proteins, enzymes, glycoproteins, and hydrocarbons. Cannabinoids and terpenes, in particular, have shown great potential in terms of medicinal value.

The Endocannabinoid System

The endocannabinoid system (ECS) consists of the two known cannabinoid receptors, CB1 and CB2, the CB receptor ligands, 2-AG and AEA, as well as the endocannabinoid synthesizing and degrading enzymes FAAH and MAGL. Other receptors, such as TRPV1, are closely related to the CB receptors and may explain the allosteric/synergistic effects exhibited. These allosteric/synergistic effects are a direct result of the various cannabinoids and terpenes found within the cannabis plant. The ECS has been implicated in a wide variety of physiological and pathophysiological processes including neural development, immune function, inflammation, appetite, metabolism and energy homeostasis, cardiovascular function, digestion, bone development and bone density, synaptic plasticity and learning, pain, reproduction, psychiatric disease, psychomotor behavior, memory, wake/sleep cycles, and the regulation of stress and emotional state. Therefore, cannabinoids (and other allosteric compounds such as terpenes) can theoretically be used as novel therapeutics in any disease in which any of the previously mentioned processes are affected. Such diseases and ailments include but are not limited to: nausea and vomiting, wasting syndrome (AIDS), lack of appetite (exhibited in cancer and AIDs patients as well as patients suffering from anorexia nervosa), multiple sclerosis, spinal cord trauma, epilepsy, pain, arthritis (and other musculoskeletal disorders), movement disorders, glaucoma, asthma, hypertension, psychiatric disorders, Alzheimer's and dementia, general inflammation, gastrointestinal disorders, and very likely, many, many more.

Phytocannabinoids, such as THC and CBD, are molecules that target cannabinoid receptors found throughout the body, providing relief to an array of symptoms including pain, nausea, and inflammation. The most common cannabinoids found in cannabis are tetrahydrocannabinol (THC), cannabidiol (CBD), and cannabinol (CBN). The network of cannabinoid receptors found throughout the body is known as the endocannabinoid system. Phytocannabinoids, cannabinoids that originate from plant sources, mimic the actions of endocannabinoids, cannabinoids synthesized naturally in the body. For example, anandamide, is an endocannabinoid that is released post-workout and found to be responsible for the "runner's high" exhibited. Anandamide does so through interactions with endocannabinoid system, just like THC and CBD.

Tetrahydrocannabinol (THC), Cannabidiol (CBD), and Cannabinol (CBN)

Tetrahydrocannabinol (THC) is the primary psychoactive compound found in cannabis. This molecule is by far the most well studied and understood component of cannabis. It is extremely safe from a toxicological perspective; not a single case of overdose has been attributed to THC (or to cannabis as a whole) despite its widespread use. Effects include analgesic, muscle relaxant, antispasmodic, bronchodilator, neuroprotective antioxidant, antiemetic, antipruritic agent in cholestatic jaundice, anti-inflammatory (20 times as effective as aspirin and 2 times as effective as hydrocortisone, added benefit: no COX-1 or COX-2 inhibition). THC induces euphoria and appetite stimulation. Extremely high doses can cause adverse effects such as paranoia, auditory and visual hallucinations, and temporary psychosis. It should be noted that these adverse effects are often negated through the entourage/synergistic effects of the phytochemicals in cannabis such as terpenes and other less prevalent cannabinoids. THC has also been shown to help reduce tic severity in Tourette's syndrome and has shown potential in treating glaucoma (reduce intraocular pressure).

Cannabidiol (CBD) is one of the principal cannabinoids found in cannabis and is largely considered to the most medically significant. CBD is non-psychoactive, meaning that unlike THC, CBD does not produce a high. CBD indirectly stimulates the endocannabinoid system, causing broad and complicated effects that have been shown to mitigate some of the negative effects of THC and other cannabinoids, contributing to the entourage/synergistic effect. Effects: modulates THC-associated adverse effects (ie. anxiety, tachycardia, hunger, and sedation), analgesic, neuroprotective antioxidant, anticonvulsant (effects on par with Dilantin—standard antiepileptic drug), antiemetic, sedative, anti-anxiety, anti-psychotic, antidepressant, anti-inflammatory, anti-tumor (prevents spread of breast cancer and many other cell lines while preserving healthy cells), shown to help rheumatoid arthritis, improves mood, displays powerful activity against methicillin-resistant *Staphylococcus aureus* (MRSA), reduces risk of stroke, ability to affect improvement in cognition, reduces acne, and acts as an immunomodulator. CBD also shows potential in the treatment of multiple sclerosis, Parkinson's disease, Alzheimer's, sleep disorders, psychotic symptoms of schizophrenia, and in fear reduction. It should also be noted that a lot of these ailments and conditions have very poor prognoses. At the very least, cannabis can be used to improve the quality of life in these patients.

Phytocannabinoids, such as THC and CBD, are molecules that target cannabinoid receptors found throughout the body providing relief to an array of symptoms including pain, nausea, and inflammation. Extremely high doses of THC can cause adverse effects such as paranoia, auditory and visual hallucinations, and temporary psychosis. It should be noted that these adverse effects are often negated through the entourage/synergistic effects of the phytochemicals in cannabis such as terpenes and other less prevalent cannabinoids.

For example, CBD has been shown to modulate THC-associated adverse effects such anxiety, tachycardia, hunger, and sedation. Other phytochemicals found within cannabis may have similar effects that will not only result in a marked potency increase but will also increase the safety of these formulations as well as reducing any of the negative/undesirable effects that result from primary constituents.

Cannabinol (CBN) is another principal cannabinoid; it is shown to have very mild psychoactive effects. Research shows that THC can naturally degrade into CBN over a long period of time and as a result of improper storage. Effects: immunomodulator, analgesic, anticonvulsant, anti-inflammatory, and also displayed powerful activity against methicillin-resistant Staphylococcus aureus (MRSA), shown to help treat burns, promotes bone formation/growth, inhibits cancer resistance protein (making chemotherapy more effective). CBN has been shown to increase the sedation effects of THC. Research also shows that CBN can effectively reduce intraocular pressure (similar to THC), making it an ideal therapeutic in the case of ocular diseases, such as glaucoma.

Each one of the various cannabinoids found in cannabis has its own medical benefits. Research shows that when they work in unison, and with other compounds in cannabis such as terpenes, they achieve the entourage effects—wherein cannabis's medical efficacy and safety is increased many times over.

Terpenes

Terpenes are a classification of organic molecules that are found in a wide variety of plants and animals. These molecules are known for their characteristic scents and flavors. The varying terpene concentrations found in cannabis directly influence the resulting taste and smell, as well as the observed effects. Even a small variation in terpene concentration can cause noticeable differences in the entourage/synergistic effects of cannabis.

Terpenes are an important component to the overall cannabis experience, not only influencing a strain's taste and smell but also influencing its effects on the mind and body. The total effect of all of the components in cannabis is referred to as the "entourage effect." This documented phenomenon is what distinguishes one strain from another, and research shows that it relies heavily on the physiological effects produced by terpenes. Over 100 different terpenes have been identified in cannabis; and despite not being quite as popular or as well-studied as cannabinoids, these diverse molecules are instrumental in delivering the physiological and psychoactive effects of cannabis.

Products of Cannabis and Methods of Administering Cannabis

Cannabis edibles or cannabis infused pharmaceuticals for oral administration are often associated with the following problems: undesirable cannabis taste, high in calorie content, contain gluten, contain animal byproducts, they do not account for the entourage effect, and they do not effectively circumvent the hepatic first pass effect.

Orally administered cannabis-based pharmaceuticals such as Marinol, which contains a single cannabinoid: delta-9-tetrahydrocannabinol, do not effectively utilize all of the medically viable compounds found within the cannabis plant. This neglects to take into account the entourage effect, a scientifically proven phenomenon wherein several compounds found in natural herbal remedies, such as cannabis, work in a synergistic capacity with primary compounds, such as THC in the case of cannabis. This effect is a product of the combined physiological and psychoactive properties of the components of natural herbal remedies, such as cannabis, in order to maximize medical efficacy and safety. Research shows that these synergistic effects lead to a three to four time increase in medical efficacy; meaning a representative/total/complete cannabis extract will be three to four times as effective as a THC-only extract. Studies also show that these synergistic compounds help mitigate some of the negative side effects of primary constituents, such as THC in the case of cannabis. This poly-pharmacological effect is a recognized and accepted theory in peer-review scientific literature. It is important to note that an underlying tenant of herbal remedies, such as cannabis, is that they often contain secondary compounds, such as terpenes, flavonoids, and other cannabinoids, that work synergistically with primary compounds, such as THC.

Furthermore, Marinol is composed of sesame seed oil, THC extract, and gel capsules. This significantly limits the absorbance of the THC and other medically viable compounds found in cannabis. By failing to factor in the hepatic first pass effect the current state of the art fails to capitalize on known methods of increasing orally administered pharmaceutical potency and efficacy. This oversight leads to a reduced efficacy and absorbance of the medically viable compounds found in cannabis. The hepatic first pass effect can be explained as a loss of drug potency and concentration before it reaches systemic circulation. After entering the digestive system and the hepatic portal system, the drug in question is carried through the portal vein and into the liver before it is distributed throughout the body. The liver notices that this is a drug and not the nutrients it is used to and places the drug on a metabolization path that greatly reduces the drug's absorption in the body. This effect is mediated by four primary systems: enzymes of the gastrointestinal lumen, gut wall enzymes, bacterial enzymes, and hepatic enzymes.

The Cannabis genus: including cannabis sativa, cannabis indica, and cannabis ruderalis species (and the seven subspecies) and their cross breeds (including established strains) in both female and male varieties, have been shown to contain chemical compounds that have both psychotropic and medicinal effects.

For centuries, the primary method of cannabis consumption has been smoking. Research shows us that smoking anything has a marked detrimental effect on the respiratory system. Furthermore, as cannabis becomes a widely accepted medicine, patients and doctors alike are seeking drug delivery methods that can optimize efficacy, potency, and duration without exerting any adverse effects on the patient. Other forms of ingestion include: oral, suppositories, inhalers, vaporization, topical, sublingual, and many more.

Smoking cannabis is a terrible delivery system for the medically viable components found in cannabis because it is inefficient, harmful to the patient, and because it does not provide accurately dosed cannabis. In practice, only 25-27% of the medically viable compounds found in cannabis are absorbed and delivered to systemic circulation making this method largely inefficient. Smoking anything introduces tar and carcinogens into the respiratory tract and is therefore harmful to the patient or user. The tar, carbon monoxide, ammonia, oxides of nitrogen, and hydrogen cyanide involved with smoking any plant material make it an extremely poor choice for drug delivery. Lastly, smoking does not provide the patient nor the doctor with any reasonable information as to the dosage consumed. The bioavailability of smoked cannabis can vary greatly and depends on depth of inhalation, puff duration, and breath-hold. There are too many variables involved for this to be a reliable drug delivery system.

A common alternative to smoking cannabis is oral administration, or eating it. There are three main drawbacks to this method of ingestion and the present invention addresses all of these issues.

Firstly, edibles and orally administered cannabis-infused pharmaceuticals are notoriously inefficient. This is largely due to the hepatic first pass effect discussed at length in the Background of the Invention section. Embodied herein are at least three methods of overcoming these issues: (1) the inclusion of surfactants (such as soy lecithin) helps emulsify the mixture causing a more uniform distribution of the active ingredients and causing the lipids utilized to bind to the medically viable compounds of interest at a greater rate—causing a marked increase in potency, efficacy, and onset, (2) nutrients (such as alcohols, fats, proteins, and carbohydrates) help "trick" the liver into recognizing the incoming substance as food or nutrients and therefore decreases the prevalence of the hepatic first pass effect, and (3) multiple iterations of heating and cooling that have been shown to break cannabinoid clusters and lead to a more potent and effective end product.

The second drawback when it comes to edibles and cannabis infused pharmaceuticals is the slow onset. The present invention's use of nutrients and surfactants does shorten the onset time but not to a significant degree.

The third drawback, and the most common complaint from users and patients who consume cannabis edibles or cannabis infused pharmaceuticals, is the taste. The present invention completely nullifies this complaint as the present invention is presented in the form of a gelatin capsule and is therefore tasteless as the user administers it.

Other drawbacks associated with most cannabis edibles and cannabis infused pharmaceuticals: high in calorie content, contain animal byproducts, contain gluten, high in sodium, religious dietary restrictions, contain food allergens, and they often ignore the entourage effect. In regards to the high calorie content, embodied herein are low calorie and no calorie compositions (due to their size vs. drug content ratio). In regards to containing gluten, embodied herein are gluten free compositions to ensure that patients with gluten intolerance can still use cannabis infused pharmaceuticals and cannabis edibles. In regards to containing high sodium contents, embodied herein are compositions that are sodium free. In regards to containing animal byproducts, embodied herein are compositions that are vegan, which ensures no animal byproducts are used in the production of this cannabis edible or cannabis infused pharmaceutical. In regards to religious dietary restrictions, embodied herein are compositions that are of the kosher and halal varieties, which ensure that patients and users of all religious backgrounds can, in good faith, consume the proposed cannabis edible or cannabis infused pharmaceutical. In regards to the food allergens, embodied herein are compositions that are allergen-free version that are completely void of the most common allergens such as, but not limited to, peanuts, soy, milk, egg, etc., thus ensuring that people with food allergies can safely consume cannabis edibles and cannabis based pharmaceuticals. Lastly, regarding the disregard of the entourage effect, as detailed earlier in this section, embodied herein are compositions that are the complete/full/representative cannabis extraction, which therefore makes full use of the entourage effect.

In the state of art, orally administered cannabis-based pharmaceuticals such as Marinol, which contains a single cannabinoid: delta-9-tetrahydrocannabinol, do not effectively utilize all of the medically viable compounds found within the cannabis plant. This neglects to take into account the entourage effect, a scientifically proven phenomenon wherein several compounds found in natural herbal remedies, such as cannabis, work in a synergistic capacity with primary compounds, such as THC in the case of cannabis. This effect is a product of the combined physiological and psychoactive properties of the components of natural herbal remedies, such as cannabis, in order to maximize medical efficacy and safety. Research shows that these synergistic effects lead to a three to four time increase in medical efficacy; meaning a representative/complete cannabis extract will be three to four times as effective as a THC-only extract. Studies also show that these synergistic compounds help mitigate some of the negative side effects of primary constituents, such as THC in the case of cannabis. This poly-pharmacological effect is a recognized and accepted theory in peer-review scientific literature. It is important to note that an underlying tenant of herbal remedies, such as cannabis, is that they often contain secondary compounds, such as terpenes, flavonoids, and other cannabinoids, that work synergistically with primary compounds, such as THC.

Also, the prior art only mentions *cannabis sativa*. The *Cannabis* genus: including *cannabis sativa, cannabis indica*, and *cannabis ruderalis* species (and the seven subspecies) and their cross breeds (including established strains) in both female and male varieties, have been shown to contain chemical compounds that have both psychotropic and medicinal effects.

For oral administration, the instant composition can be also formulated readily by combining the active compounds with pharmaceutically acceptable carriers well known in the art. Such pharmaceutically acceptable carriers enable the compounds of the present embodiments to be formulated as tablets, pills, dragees, capsules, liquids, gels, syrups, slurries, suspensions and the like, for oral ingestion by a patient to be treated. Pharmaceutical formulations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Alternatively, the formulations may be presented in a form suitable for once-daily, once-weekly or once-monthly administration; for example, an insoluble salt of the active compound may be adapted to provide a preparation for intramuscular injection. The pharmaceutical formulations described herein can be administered to a patient per se, or in pharmaceutical formulations where they are mixed with other active ingredients, as in combination therapy, or suitable pharmaceutically acceptable carriers or excipient(s). Techniques for formulation and administration of the compounds of the instant application may be found in "Remington's Pharmaceutical Sciences," Mack Publishing Co., Easton, Pa., 18th edition, 1990.

The daily dosage of the products may be varied over a wide range; e.g., from about 10 to about 10,000 mg per adult human per day. For oral administration, the formulations are preferably provided in the form of tablets containing about 0.1, 0.25, 0.5, 1.00, 5.00, 10.0, 15.0, 25.0, 50.0, 100, 200, 300, 400, 500, 600, 700, 800, 900 1000, 2000, 3000, 4000, 5000, 6000, 7000, 8000, 9000 or 10,000 milligrams of the active ingredient for the symptomatic adjustment of the dosage to the patient to be treated. The instant pharmaceutical formulations typically contain from 10 mg to about 2000 mg of the instant compounds, preferably, from about 50 mg to about 1000 mg of active ingredient. An effective amount of the instant compounds is ordinarily supplied at a dosage level of from about 0.002 mg/kg to about 150 mg/kg of body weight per day. Preferably, the range is from about 0.02 to about 80 mg/kg of body weight per day, and especially from about 0.2 mg/kg to about 40 mg/kg of body weight per day. The compounds may be administered on a regimen of about 1 to about 10 times per day. It is understood that the dosage may vary widely from person to person based on numerous factors.

Entourage Effect

The entourage effect, or the combinatory effects of the phytochemicals (at varying ratios) found in cannabis, is generally a more supported notion for therapeutic uses rather than isolated cannabinoids. Isolated cannabinoids, such as CBD, do exhibit efficacy on their own (in the case of schizophrenia, for example) but the interactions among all of the various phytochemicals in cannabis produce a much more effective and safe drug for patients. Isolated THC (Marinol) is known to produce extremely adverse effects in patients, so much so that some patients stop taking the drug (anorexia study). The entourage effect mitigates the negatives and highlights the positives. In order to truly treat a disease or ailment, the entourage effect can be fine-tuned to meet the needs of the patient.

Terpenes and cannabinoids have been shown to be largely responsible for the beneficial effects of cannabis. In fact, it is the varying concentrations medically viable compounds that result in different strains (genotypes) and their resulting chemotypes (which can vary with grow conditions). Even a small variation in terpene or cannabinoid concentration can cause noticeable differences in the entourage/synergistic effects of cannabis. This documented phenomenon is what distinguishes one strain from another, and research shows it relies heavily on the physiological effects produced by terpenes. Over 100 different terpenes have been identified in cannabis; and despite not being as well-studied as cannabinoids, these diverse molecules are instrumental in delivering the physiological and psychoactive effects of cannabis.

Figure 20:
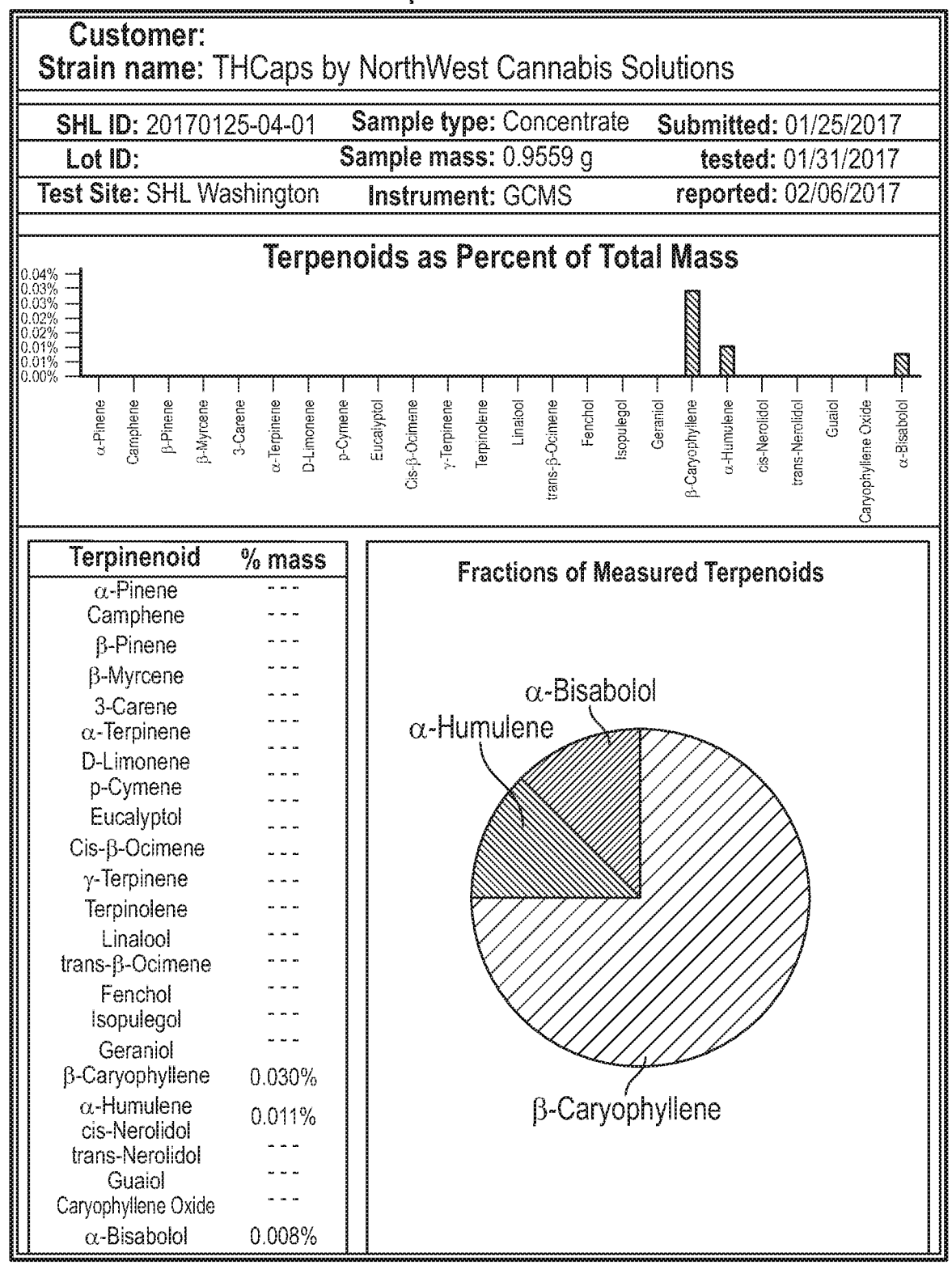
FIG. 20 Terpene analysis of THCaps by NorthWest Cannabis Solutions—a THC only formulation like Marinol.
Figure 23:
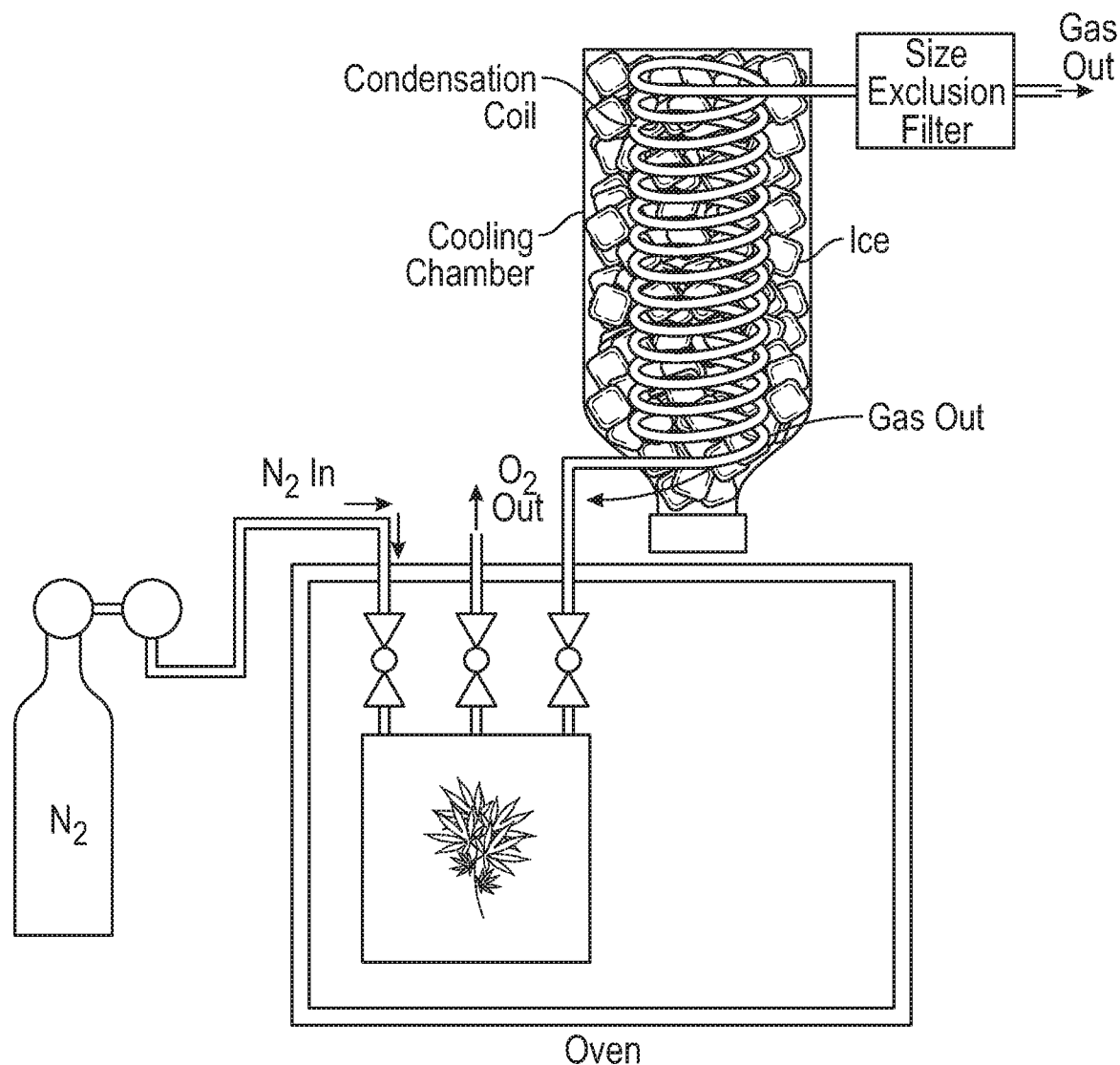
FIG. 23 Depicts one embodiment of producing a cannabis extract using a size exclusion filter and a coil to condense terpenes, compounds of pharmaceutical interest, and compounds of organoleptic interest.

In the solvent based extractions detailed above, the residual solvents are purged from the extract. The primary method of purging the residual solvents utilized in the cannabis extract industry is through use of a purge/vacuum oven/chamber. A purge/vacuum oven is generally operated in the following manner: the oven contains racks where trays of unpurged cannabis extracts are placed. The purge/vacuum oven can then be set to a variety of temperature and pressure programs aimed at accelerating the purge process to bring the amounts of residual solvents in these extract to below action limits set by the state in which the processor/extractor operates. The main and obvious drawback that comes with using purge/vacuum ovens/chambers is that they do not exclusively purge solvents; they also purge other volatile compounds such as terpenes (and other compounds of pharmaceutical/organoleptic interest) as demonstrated in FIGS. 19 and 20. This process can strip the cannabis extract of many volatile pharmaceutical components, thereby lowering the overall pharmaceutical efficacy and potency of the cannabis extract.

Embodiments of Methods and Apparatuses

Disclosed herein are methods of cannabis extraction in which these compounds (including but not limited to cannabinoids, terpenes, etc.) that contribute to the entourage effect are retained. In some embodiments, the apparatus disclosed in FIGS. 2A, 2B, and 2C is used to retain these compounds through the use of a size exclusion filter wherein compounds of a certain size are retained in the chamber/reaction vessel and compounds smaller than a certain size will pass through the size exclusion filter and exit the chamber/reaction vessel. Leveraging the physical differences between compounds allow for the formulation of cannabis products with unprecedented quality as there will be virtually no loss of the compounds in cannabis and cannabis extracts that contribute to its pharmaceutical efficacy (compounds that contribute to the entourage effect).

The use of any/all medically viable compounds found within the cannabis plant leads to the effective utilization of the entourage effect, ensuring a safer and more effective pharmaceutical formulation. These compounds activate and regulate the endocannabinoid system resulting in a wide variety of effects and possible therapeutic applications. The ECS has been implicated in a wide variety of physiological and pathophysiological processes including but not limited to neural development, immune function, inflammation, appetite, metabolism and energy homeostasis, cardiovascular function, digestion, bone development and bone density, synaptic plasticity and learning, pain, reproduction, psychiatric disease, psychomotor behavior, memory, wake/sleep cycles, and the regulation of stress and emotional state. Therefore, cannabinoids (and other allosteric compounds such as terpenes) can theoretically be used as novel therapeutics in any disease in which any of the previously mentioned processes is affected. Such diseases and ailments include but are not limited to: nausea and vomiting, wasting syndrome (AIDS), lack of appetite (exhibited in cancer and AIDS patients as well as patients suffering from anorexia nervosa), multiple sclerosis, spinal cord trauma, epilepsy, pain, arthritis (and other musculoskeletal disorders), movement disorders, glaucoma, asthma, hypertension, psychiatric disorders, dementia, general inflammation, gastrointestinal disorders, acute stress disorder; affective disorders, including depressive disorders (major depressive disorder, dysthymia, childhood depression, atypical depression, bipolar disorder, mania and hypomania) and anxiety disorders (generalized anxiety disorder, social anxiety disorder, phobias, obsessive compulsive disorder, panic disorder, post-traumatic stress disorder); premenstrual dysphoric disorder (also known as pre-menstrual syndrome); psychotic disorders, such as brief psychotic disorder, schizophrenia, psychotic mood disorder (depression and/or mania); attention deficit disorder (with and without hyperactivity); obesity, eating disorders such as anorexia nervosa and bulimia nervosa; vasomotor flushing; cocaine and alcohol addiction; sexual dysfunction and related illnesses; acute and chronic pain syndromes, as exemplified by fibromyalgia, chronic low back pain, trigeminal neuralgia; visceral pain syndromes, such as irritable bowel syndrome, noncardiac chest pain, functional dyspepsia, interstitial cystitis, essential vulvodynia, urethral syndrome, orchialgia, temperomandibular disorder, atypical face pain, migraine headache, and tension headache; functional somatic disorders, for example, chronic fatigue syndrome; neurologic disorders including seizure disorder, Tourette Syndrome, Parkinson's Disease, Huntington's Chorea, Alzheimer's Disease, subcortical and other dementias, Tardive Dyskinesia, Rett Syndrome, amyotrophic lateral sclerosis and others. It should also be noted that a lot of these ailments and conditions have very poor prognoses. At the very least cannabis can be used to improve the quality of life in these patients.

Embodiments of the cannabis extraction process disclosed herein include the use methods and apparatuses that preserve important pharmaceutical components of the cannabis extraction process. (See, for example, FIGS. 2A, 2B, 2C, and 3).

In some embodiments, all species or any combination of various species of *cannabis* are used in the extraction process including *cannabis sativa, cannabis indica*, and *cannabis ruderalis* species (and the seven sub-species) and their cross breeds (including established strains) in both female and male varieties. In some embodiments, a representative/total/complete preparation made using the apparatus depicted in FIGS. 2A, 2B, and 2C is provided. A variety of extraction mediums may be used, including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) of cannabis and any/all medically viable compounds found therein (including but not limited to cannabinoids, nitrogenous compounds, amino acids, proteins, enzymes, glycoproteins, hydrocarbons, simple alcohols, aldehydes, ketones and acids, fatty acids, simple esters and lactones, steroids, terpenes, non-cannabinoid phenols, flavonoids, vitamins, and pigments) and its species (including but not limited to *cannabis sativa, cannabis indica, cannabis ruderalis*—and any/all subspecies and any/all cross breeds thereof and any/all established strains—in both male and female varieties—using both live and dried cannabis plant material) and the subsequent conversion of these extracts into pill-able forms for oral administration (immediate and extended release).

In some embodiments, surfactant(s)/emulsifier(s) and nutritional compounds are used in order to increase the bioavailability and subsequent absorption of these orally administered cannabis pills/capsules, and the medically viable compounds found therein as a result of a total cannabis extraction, within the mammalian gastrointestinal tract (effectively bypassing the hepatic first pass effect). Varieties will include but will not be limited to: Vegan, kosher, halal, gluten free, extremely potent, CBD rich, low potency, non-decarboxylated (non-psychoactive), live plant material, allergen-free, extended release, very low or sodium free, established cannabis strains, and more. The Apparatus depicted in FIGS. 2A, 2B, and 2C may be used to retain compounds of pharmaceutical interest (during the cannabis extract purge process and the cannabis/cannabis extract decarboxylation process) by utilizing a size exclusion filter. Thus, the apparatus leverages the physical differences between compounds the seeking to be retained and the compounds that should be purged The following sections provide description of further embodiments. Following this, descriptions of non-limiting examples are provided.

Embodiments of Methods of Extracting Cannabis

In some embodiments, a method of cannabis extraction is provided. The method comprises (i) adding any amount of at least one species of *cannabis* plant or any amount of an extract of at least one species of *cannabis* plant to a reaction chamber, (ii) optionally producing cannabis extracts through extracting cannabis from the amount of at least one species of *cannabis* plant in the chamber, (iii) removing byproducts from the reaction chamber that are produced from extracting cannabis, (iv) retaining compounds within the chamber derived from cannabis. The chamber comprises a filter in which the pores of the filter allow for removal from the reaction chamber of byproducts of the extraction process but prevent removal of compounds derived from cannabis.

Any species of *cannabis*, whether it is a currently known species or a species to be discovered in the future, can be added to the reaction chamber in step (i). Any number of species can be added to the reaction chamber in a given reaction, up to and including adding all of the species of *cannabis*. In some embodiments, the species of *cannabis* added to the reaction chamber comprise *Cannabis sativa, Cannabis indica*, and *Cannabis ruderalis*. In some embodiments, any one of these species is added to the reaction chamber. In some embodiments, any two of these species are added to the reaction chamber. In some embodiments, all three of these species are added to the reaction chamber.

In some embodiments, the cannabis used in the extraction process is a live extract. In some embodiments, the cannabis used in the extraction process is a dried and/or cured extract.

In some embodiments, the reaction chamber used in the method is an airtight reaction chamber.

In some embodiments, the extraction step (ii) comprises a solvent based extraction method. Any solvent known in the art that is used to extract cannabis may be used to in the extraction step. In some embodiments, the solvent used is, for example, iso-propyl, methanol, n-propyl alcohol, propane, butane, iso-butane, methanol, and ethanol.

In some embodiments, the extraction step (ii) does not use a solvent. In some embodiments, the extraction is a heat extraction, an unheated extraction, a cold water extraction, a $CO_2$ extraction, and a rosin tech extraction.

In some embodiments a method is provided that comprises a optional cannabis extraction step and a decarboxylation step. Any temperature/time period known in the art sufficient to decarboxylate cannabis can be used in the decarboxylation step. In some embodiments, the decarboxylation step comprises using an enzyme or cofactor that catalyzes the decarboxylation step, for example, a decarboxylase. In some embodiments, $H_2O$ is used as a catalyst of the decarboxylation reaction. In some embodiments, the decarboxylation step occurs in the presence of an inert gas.

The inert gas may be any of the noble gas including helium, neon, argon, krypton, xenon, and radon.

In some embodiments, the cannabis extraction method further comprises the step of treating the reaction chamber with an inert gas prior to the decarboxylation reaction.

The decarboxylation step will result in the release of $CO_2$. In some embodiments, the $CO_2$ is released from the reaction chamber by passing the $CO_2$ through the filter.

In some embodiments a non-solvent based extraction process is used in step (ii). In some embodiments, a cold water extraction is used. In some embodiments, a heat extraction is used.

In some embodiments, a method of cannabis extraction is provided wherein the compounds retained within the chamber in step (iv) that are derived from cannabis comprise cannabinoids. In some embodiments, a method of cannabis extraction is provided wherein the compounds retained within the chamber in step (iv) that are derived from cannabis comprise terpenes. In some embodiments, the compounds retained within the chamber comprise cannabinoids and terpenes.

In some embodiments, a method of cannabis extraction is provided wherein the compounds retained within the chamber in step (iv) that are derived from cannabis comprise cannabinoids, terpenes/terpenoids, amino acids, nitrogenous compounds, simple alcohols, aldehydes, ketones, esters, lactones, and acids, fatty acids, steroids, non-cannabinoid phenols, pigments, flavonoids, vitamins, proteins, enzymes, glycoproteins, and hydrocarbons. The compounds retained within the chamber may comprise any one or more of these compounds, in any combination.

In some embodiments, a method of cannabis extraction is provided wherein the compounds retained within the chamber in step (iv) that are derived from cannabis comprise the at least 545 distinct compounds in cannabis. The compounds retained within the chamber may comprise any one or more of the at least 545 distinct compounds, in any combination. In some embodiments, the compounds derived from cannabis in step (iv) comprise cannabinoids, nitrogenous compounds, amino acids, proteins, enzymes, glycoproteins, hydrocarbons, simple alcohols, aldehydes, ketones and acids, fatty acids, simple esters and lactones, steroids, terpenes, non-cannabinoid phenols, flavonoids, vitamins, and pigments, in any combination. In some embodiments, the compounds derived from cannabis in step (iv) comprise any one more of cannabinoids, nitrogenous compounds, amino acids, proteins, enzymes, glycoproteins, hydrocarbons, simple alcohols, aldehydes, ketones and acids, fatty acids, simple esters and lactones, steroids, terpenes, non-cannabinoid phenols, flavonoids, vitamins, and pigments, in any combination.

In some embodiments, a method is provided which comprises extracting cannabis from plant material (live or dried) using a variety of extraction protocols (including but not limited to: cold water extraction and dry sift (hash), CO2, hydrocarbons (including but not limited to: butane, propane, hexane), alcohol (including but not limited to: ethanol, iso-propyl, methanol, n-propyl alcohol), and rosin tech (heated or unheated pressed extraction)) from any/all *cannabis* species (including but not limited to *cannabis sativa, cannabis indica, cannabis ruderalis*—and any/all subspecies and any/all cross breeds thereof and any/all established strains—in both male and female varieties—using both live and dried cannabis plant material).

The resulting extract is composed of one or more of the following compounds, in any combination: cannabinoids, terpenes, and any/all medically viable compounds found therein (including but not limited to cannabinoids, nitrogenous compounds, amino acids, proteins, enzymes, glycoproteins, hydrocarbons, simple alcohols, aldehydes, ketones and acids, fatty acids, simple esters and lactones, steroids, terpenes, non-cannabinoid phenols, flavonoids, vitamins, and pigments).

In some embodiments, a method of preserving terpenes (and other compounds of pharmaceutical and organoleptic interest) in the decarboxylation process and extraction purge process is provided. In some embodiments the method utilizes a chamber/reaction vessel that makes use of a size-exclusion filter (filtration based on molecular dimensions) as a means of retaining terpenes (and other compounds of pharmaceutical/organoleptic interest) while allowing $CO_2$ (the primary byproduct of cannabinoid decarboxylation—i.e. activation of the cannabinoids) and residual solvents (including but not limited to: alcohols—such as ethanol and alkanes—such as butane) to exit the chamber/reaction vessel.

In some embodiments a method is provided comprising condensing compounds of interest within a coil. In some embodiments the compounds condensed in the chamber comprise any one or more of terpenes, compounds of pharmaceutical interest, and compounds of organoleptic interest. In some embodiments, the coil is temperature regulated. In some embodiments, the terpenes and/or compounds are condensed within the coil immediately before the compounds contact a filter.

Any of the methods described herein for extracting cannabis may further comprise the use of a surfactant. Any of the methods described herein for extracting cannabis may further comprise the use of an emulsifier. Any emulsifier known in the art can be used. Examples of emulsifiers include but are not limited to soy lecithin, egg yolk, sodium phosphates, and sodium stearoyl lactylate, amongst others.

Embodiments of Apparatuses for Extracting Cannabis and Methods of Using the Apparatuses In some embodiments, an apparatus for extracting cannabis is provided. In some embodiments an apparatus for extracting cannabis is provided that is depicted in FIGS. 2A, 2B, and 2C. The apparatus comprises an airtight container (1) with a reaction chamber (20) and a size exclusion filter (10). The size exclusion filter comprises pores (30) that are of sufficient size to allow byproducts of a cannabis extraction process and of the decarboxylation process to pass through the filter. The size exclusion filter prevents the passage of compounds derived from cannabis.

In some embodiments the size exclusion filter with a filter size between 0.01 $Å^2$ and 100 $Å^2$, for example between 20 and 40 $Å^2$, between 22 $Å^2$ and 38 $Å^2$, between 24 $Å^2$ and 36 $Å^2$, between 26 $Å^2$ and 34 $Å^2$, between 28 $Å^2$ and 32 $Å^2$. In some embodiments the size exclusion filter is between 29 $Å^2$-31 $Å^2$. Varying the size of the filters will allow users to retain desired products within the reaction chamber while allowing unwanted byproducts to escape.

One embodiment of this use of different filter sizes is to leverage the difference in size between $CO_2$ (the most common byproduct of a decarboxylation process) and Myrcene (one of the smallest known terpenes found in cannabis) from passing through the filter. $CO_2$ has a minimum projecting area of 9.08 $Å^2$ and Myrcene has a minimum projection area of 30.96 $Å^2$. A filter embodied in the ranges above could be used that prevents the passage of Myrcene through the filter, thus retaining Myrcene in the reaction chamber, while allowing $CO_2$ to pass through the filter, thus purging $CO_2$. Further embodiments of this idea are illustrated in Table 1. As shown on Table 1, the minimum projection area of the terpenes and cannabinoids (which are non-limiting examples of compounds derived from cannabis that a user may want to retain) are larger than the maximum projection area of inert gases, residuals solvents, and product of decarboxylation (which are non-limiting examples of byproducts that a user may want to purge from the reaction chamber).

TABLE 1

| Compound Type | Compound/Element Name | Minimum Projection Area ($Å^2$) | Maximum Projection Area ($Å^2$) |
|---|---|---|---|
| Inert Gas | Helium | 6.16 | 6.16 |
| | Neon | 7.45 | 7.45 |
| | Argon | 11.1 | 11.1 |
| Residual Solvents | Propane | 18.11 | 23.67 |
| | Butane | 18.85 | 29.47 |
| | Iso-Butane | 22.11 | 29.22 |
| | Methanol | 11.18 | 15.32 |
| | Ethanol | 15.61 | 21.19 |
| Product of Decarboxylation | Carbon Dioxide | 9.08 | 14.11 |
| Terpenes | Myrcene | 30.96 | 51.62 |
| | Alpha-Pinene | 34.54 | 43.89 |
| | Linalool | 31.27 | 57.99 |
| | Caryophyllene | 44.48 | 62.5 |
| | Eucalyptol | 38.81 | 45.67 |
| | Alpha-Bisabolol | 45.45 | 72.85 |
| Cannabinoids | Tetrahydrocannabinol I | 48.89 | 100.62 |
| | Cannabidiol | 54.88 | 94.23 |
| | Cannabinol | 47.35 | 99.6 |

In some embodiments, the apparatus comprises a coil that precedes the filter. In some embodiments, the coil is temperature regulated. In some embodiments, the coil functions to condense the terpenes and other molecules of pharmaceutical and organoleptic interest before they reach the size exclusion filter.

Turning again to FIGS. 2A, 2B, and 2C, in some embodiments, the apparatus comprises a stir bar (60), for example, a magnetic stir bar. In some embodiments, a base is provided that rotates the stir bar. In some embodiments, the inner surface of the apparatus is lined with a non-stick coating Any non-stick coating known in the art can be used. Examples of a non-stick coating include but are not limited to Teflon and silicone.

An embodiment of an apparatus that combines a stir bar with a non-stick surface, can aid in facilitating the removal of cannabis extracts after any byproducts of the extraction process and/or the decarboxylation process have been removed through the size exclusion filter.

In some embodiments, the apparatus is temperature controlled. In some embodiments, the apparatus is pressure controlled. In some embodiments, the apparatus is both temperature and pressure controlled. An apparatus that is both temperature and pressure controlled can allow for multiple combinations of temperature and pressure during the cannabis extraction process and/or the decarboxylation process. For example, less heat can be utilized during a longer purge/decarboxylation duration in order to prevent any unwanted side reactions.

In some embodiments, the apparatus comprises a loading door (40) that is used for the introduction of cannabis or cannabis extracts, which can be latched shut to preserve the airtight seal of the apparatus. The dimensions of the loading door can be adjusted as needed to allow for the introduction of different amounts and different types of cannabis material into the apparatus.

In some embodiments, the apparatus comprises a steel rod (50) that is attached to the size exclusion filter and that is within the reaction chamber. In some embodiments, the steel rod passes through the center of the reaction chamber. In some embodiments, the size exclusion filter is able to move up and down on the steel rod. Moving the size exclusion filter up and down the steel rod, allows the size exclusion filter to be placed at an optimal distance from the material that is undergoing the extraction process and/or decarboxylation process.

In some embodiments, the apparatus comprises one or more valves (70) that function to introduce the inert gas into the reaction chamber. In some embodiments, the apparatus comprises two valves.

In some embodiments, methods of extracting cannabis are provided in which any of the apparatuses described herein are used. In some embodiments a method is provided comprising using any of the apparatuses described herein, comprising the steps of (i) adding any amount of at least one species of *cannabis* plant or any amount of an extract of at least one species of *cannabis* plant to a reaction chamber, (ii) optionally producing cannabis extracts through extracting cannabis from the amount of at least one species of *cannabis* plant in the chamber, (iii) removing byproducts from the reaction chamber that are produced from extracting cannabis, and (iv) retaining compounds within the chamber derived from cannabis, wherein the reaction chamber comprises a filter in which the pores allow for removal from the reaction chamber of the byproducts from the cannabis extraction process and prevent removal from the chamber of the compounds derived from cannabis.

Embodiments of Mixtures of Compounds Derived from Cannabis

In some embodiments, a mixture of compounds derived from cannabis is provided. In some embodiments, the mixture comprises any of the compounds depicted in FIGS. 4-17, in any combination.

In some embodiments, a mixture of compounds is provided that comprises at least one terpene compound derived from cannabis and at least one cannabinoid compound derived from cannabis.

In some embodiments, any of the mixtures of compounds described herein comprise at least 5 terpene compounds derived from cannabis, for example, at least 10 terpene compounds derived from cannabis, at least 15 terpene compounds derived from cannabis, or at least 20 terpene compounds derived from cannabis.

In some embodiments, the mixture of compounds comprises 24 terpene compounds derived from cannabis. In some embodiments the 24 terpene compounds comprise, α-Pinene, Camphene, β-Pinene, β-Myrcene, 3-Carene, α-Terphinene, D-Limonene, p-Cymene, Eucalyptol, cis-β-Ocimene, γ-Terpinen, Terpinolene, Linalool, trans-β-Ocimene, Fenchol, Isopulegol, Geraniol, β-Caryophyllene, α-Humulene, cis-Nerolidol, trans-Nerolidol, Guaiol, Caryophyllene Oxide, and α-Bisabolol.

In any of the embodiments of mixtures of compounds described herein, the percent mass of each terpene compound is between 0.0001% and 10%, for example between 0.0001% and 0.1%, between 0.0005% and 0.07% or between 0.001% and 0.05%.

In some embodiments, the terpene profile is similar to the profile depicted in FIG. 22.

In some embodiments, any of the mixtures of compounds described herein comprise at least 3 cannabinoid compounds derived from cannabis, for example, 7 compounds derived from cannabis. In some embodiments, the 7 cannabinoid compounds comprise: THC-A, CBL-A, 49-THC, CBN, CBC, CBG, and THCV.

In any of the embodiments of mixtures of compounds described herein, the mg/ml of each cannabinoid is between 0.0001 mg/ml and 1000 mg/ml, for example, 0.01 mg/l and 25 mg/ml or between 0.1 mg/ml and 22 mg/ml.

In some embodiments, the cannabinoid profile is similar to the profile depicted in FIG. 21.

In some embodiments, a mixture of compounds derived from cannabis is provided that comprises cannabinoids, nitrogenous compounds, amino acids, proteins, enzymes, glycoproteins, hydrocarbons, simple alcohols, aldehydes, ketones and acids, fatty acids, simple esters and lactones, steroids, terpenes, non-cannabinoid phenols, flavonoids, vitamins, and pigments. In some embodiments, a mixture of compounds derived from cannabis is provided that comprises any one or more of cannabinoids, nitrogenous compounds, amino acids, proteins, enzymes, glycoproteins, hydrocarbons, simple alcohols, aldehydes, ketones and acids, fatty acids, simple esters and lactones, steroids, terpenes, non-cannabinoid phenols, flavonoids, vitamins, and pigments, in any combination.

Figure 18:
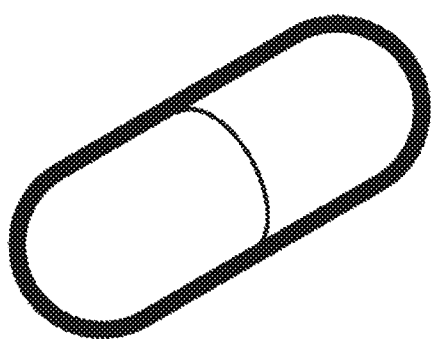
FIG. 18 depicts a visual representation of an embodiment of the final product (cannabis edible and cannabis infused pharmaceutical)

In any of the embodiments of mixtures of compounds described herein, the compounds may be contained within a capsule. In some embodiments, the capsule is a gelatin capsule that is depicted in FIG. 18.

In some embodiments, any of the capsules described herein comprises a pharmaceutical formulation. In some embodiments, any of the cannabis formulations described herein comprise a pharmaceutical formulation.

Methods of Treatment

In some embodiments, a method of treatment is provided that comprises administering a pharmaceutically acceptable amount of any of the pharmaceutical formulations described herein to a patient in need thereof. In some embodiments administering the mixture to the patient results in the patient experiencing the entourage effect.

Any of the pharmaceutical formulations described herein may be administered for the purpose of treating any one or more of the following: nausea and vomiting, wasting syndrome (AIDS), lack of appetite (exhibited in cancer and AIDs patients as well as patients suffering from anorexia nervosa), multiple sclerosis, spinal cord trauma, epilepsy, pain, arthritis (and other musculoskeletal disorders), movement disorders, glaucoma, asthma, hypertension, psychiatric disorders, Alzheimer's and dementia, general inflammation, gastrointestinal disorders.

As used herein, the term "patient" refers to the recipient of a therapeutic treatment and includes all organisms within the kingdom animalia. In preferred embodiments, the animal is within the family of mammals, such as humans, bovine, ovine, porcine, feline, buffalo, canine, goat, equine, donkey, deer and primates. In some embodiments, the animal is human.

As used herein, the terms "treat" "treating" and "treatment" include "prevent" "preventing" and "prevention" respectively.

Language of degree used herein, such as the terms "approximately," "about," "generally," and "substantially" as used herein represent a value, amount or characteristic close to the stated value, amount or characteristic that still performs a desired function or achieves a desired result. For example, the terms "approximately," "about," "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15°, 10°, 5°, 3°, 1°, 0.1°, or otherwise. Similarly, in certain embodiments, the terms "generally perpendicular" and "substantially perpendicular" refer to a value, amount, or characteristic that departs from exactly perpendicular by less than or equal to 15°, 10°, 5°, 3°, 1°, 0.1°, or otherwise.

EXAMPLES

Some aspects of the embodiments discussed above are disclosed in further detail in the following examples, which are not in any way intended to limit the scope of the present disclosure.

Example 1

Cannabis Extraction Using Hybrid Strains

Starting with cannabis plant material that originates from any and all hybrid cannabis strain (mixed breed of cannabis, including but not limited to *cannabis sativa, cannabis indica*, and/or *cannabis ruderalis*—and any/all sub species—in both male and female varieties), the sample was dried and cured (proper drying and storage protocol ensures maximal terpene content), then the medically viable compounds (primarily cannabinoids and terpenes) were extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

For solvent based cannabis extracts, the residual solvents were purged from the extract while retaining compounds of pharmaceutical and organoleptic interest. Next, the sample was decarboxylated (at a variety of temperatures (~90-180° C.). This decarboxylation was performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, *yucca* extract) were added to the decarboxylated extract (or decarboxylated plant material). The mixture was then subjected to an optional heating step temperatures (~90-180° C.). The duration of the heating step varied depending on batch size, desired characteristics of final product, and other factors. Varying the temperatures, pressures, methods, and durations of heat exposure greatly influenced the medical characteristics of the final product.

In an optional step, nutritional compounds (including but not limited to: alcohols, fats, carbohydrates, and proteins) and food coloring were added to the mixture after which the mixture was frozen. In some of the extractions, the mixture was subjected to further iterations of heating and freezing cycles. The mixture, which was a yellow/light brown/golden in color, was filtered and used to fill gelatin capsules (FIG.

18). The capsules were then stored. FIGS. 21 and 22 show the amounts and percentages of terpenes and cannabinoids that resulted from this decarboxylation method.

All ingredients may vary in ratio in final product, from 0-100% by weight. Not all ingredients or steps listed above must be performed. For example, (1) omission of nutrients does not constitute a new product and (2) omission of the freezing step does not constitute a new manufacturing process.

Example 2

Cannabis Extraction Using the *Cannabis Indicia* Strain

Starting with cannabis plant material that originates from any and all *cannabis indica* strains (and any/all subspecies— in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

Figure 3:
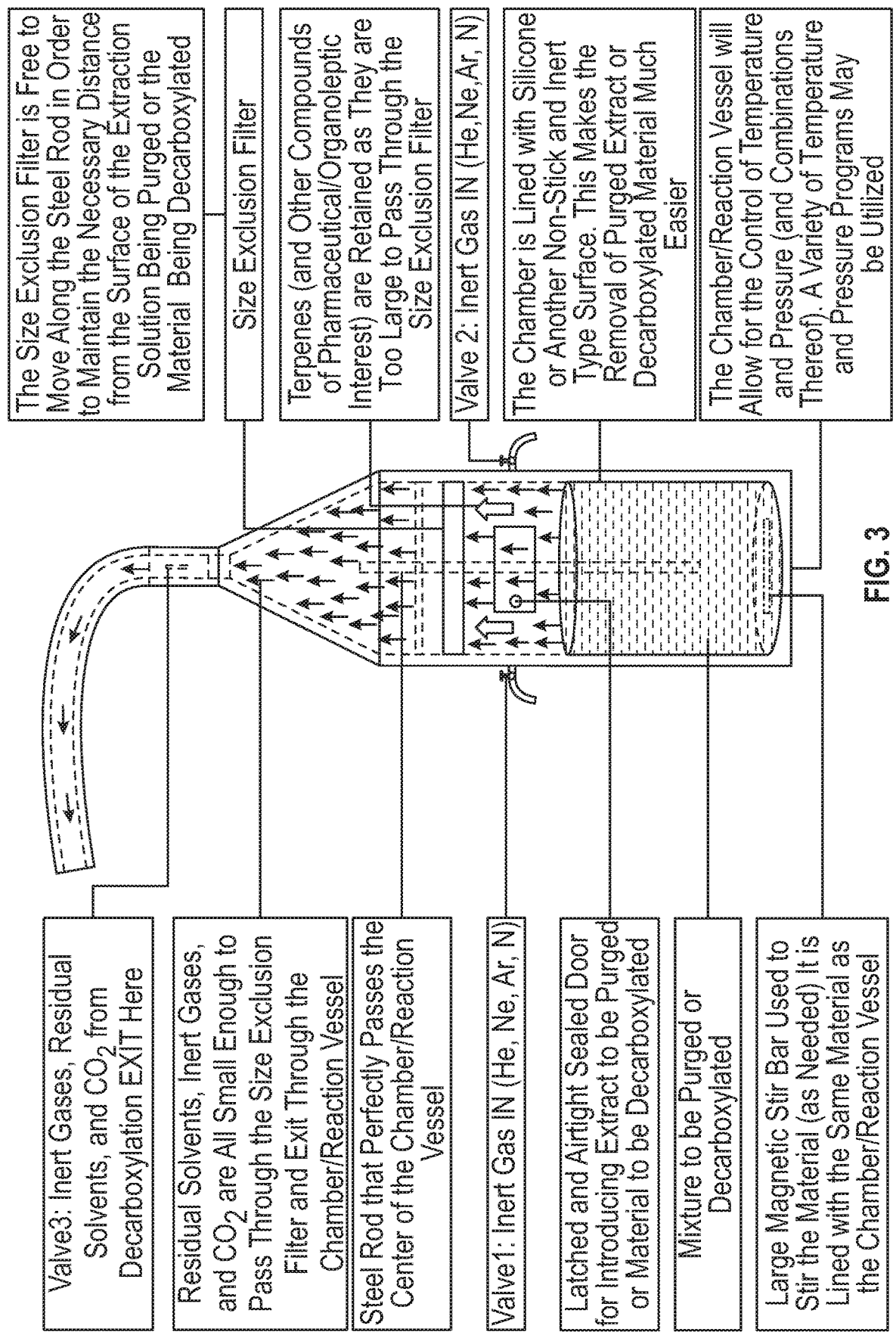
FIG. 3 depicts a schematic of an embodiment of an apparatus utilizing a size exclusion filter.
Figure 4:
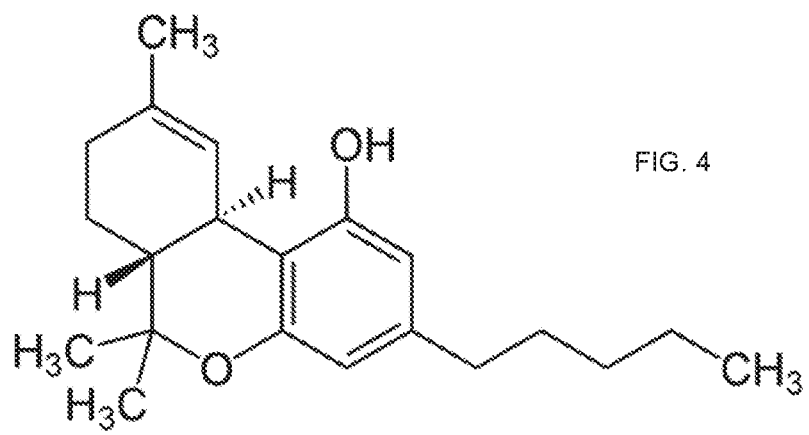
FIG. 4 depicts the molecular structure of tetrahydrocannabinol (the primary psychoactive component found in cannabis).
Figure 5:
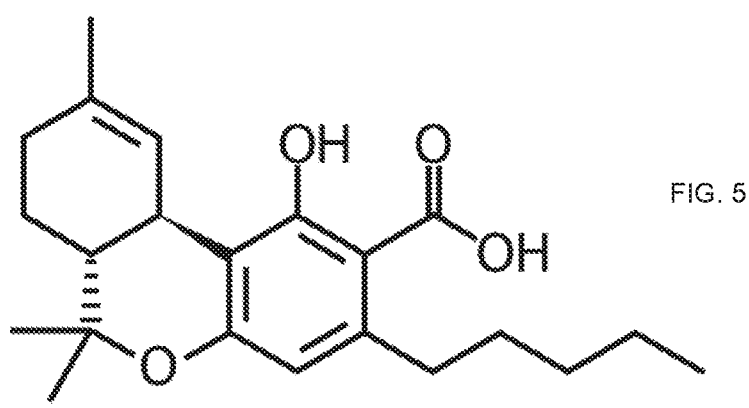
FIG. 5 depicts the molecular structure of tetrahydrocannabinolic acid.
Figure 6:
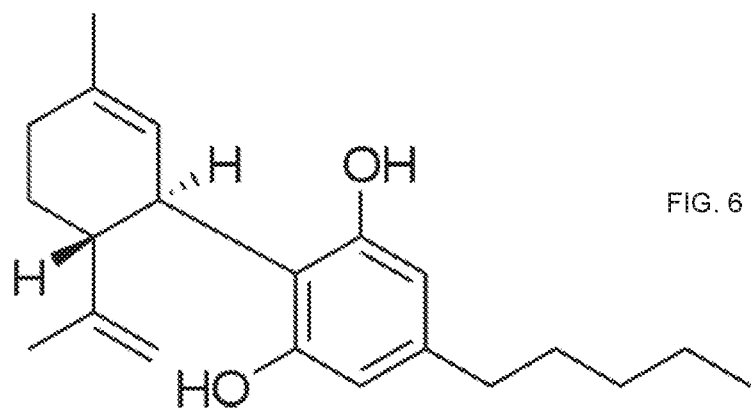
FIG. 6 depicts the molecular structure of cannabidiol.
Figure 7:
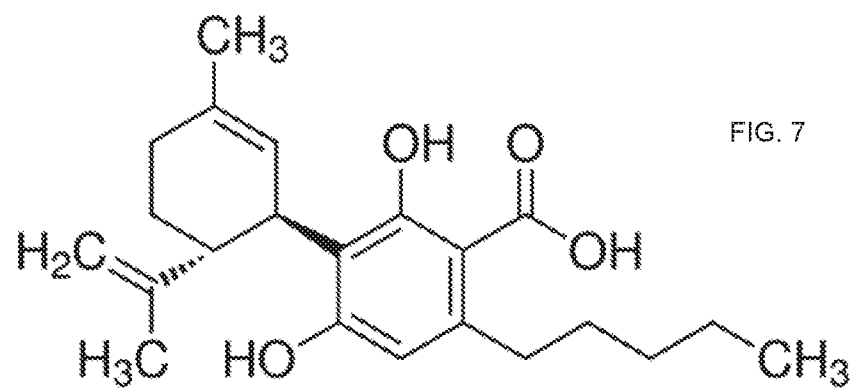
FIG. 7 depicts the molecular structure of cannabidiolic acid.
Figure 8:
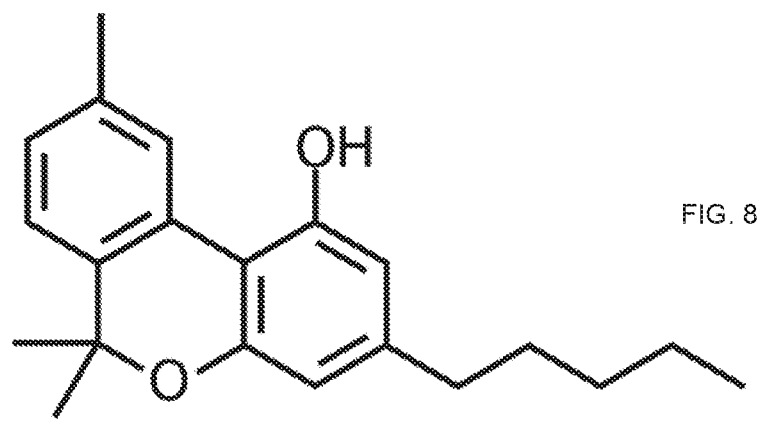
FIG. 8 depicts the molecular structure of cannabinol
Figure 9:
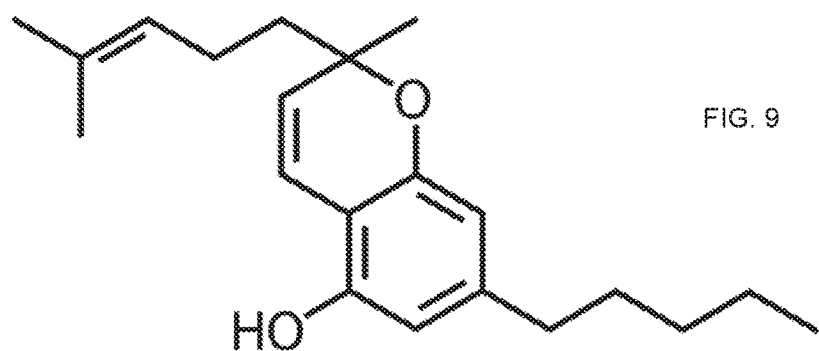
FIG. 9 depicts the molecular structure of cannabichromene.
Figure 10:
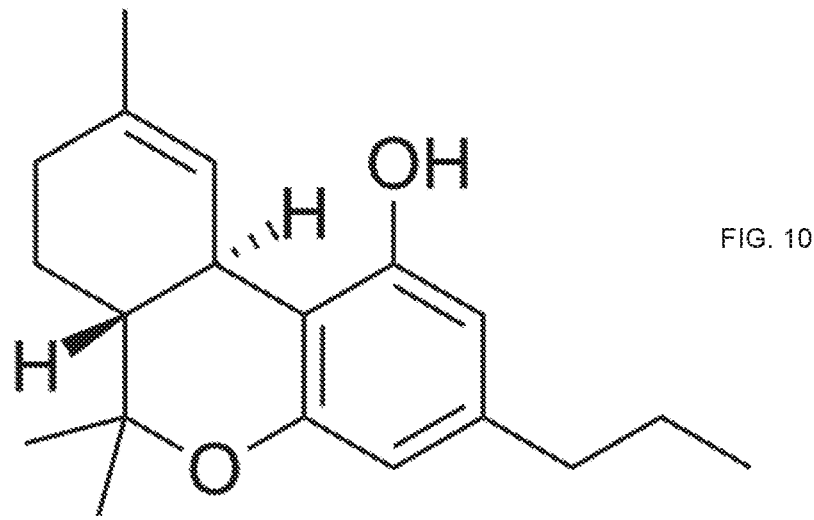
FIG. 10 depicts the molecular structure of tetrahydrocannabivarin.
Figure 11:
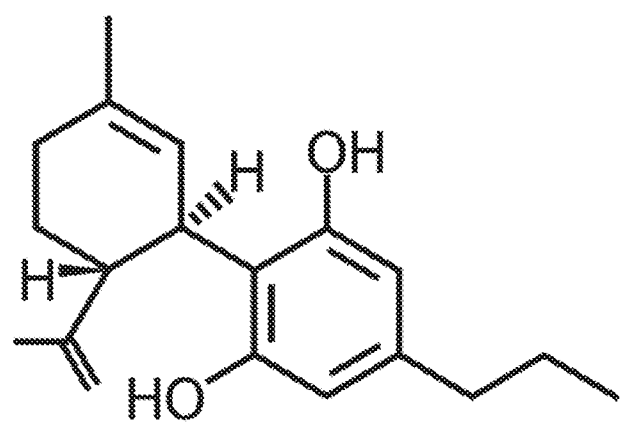
FIG. 11 depicts the molecular structure of cannabidivarin.
Figure 12:
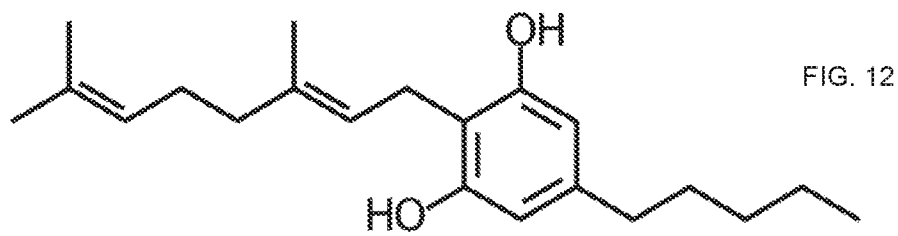
FIG. 12 depicts the molecular structure of cannabigerol.
Figure 13:
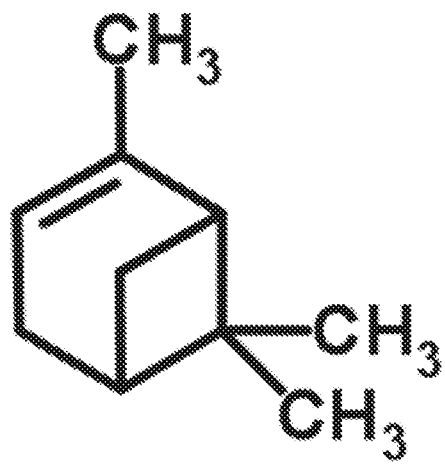
FIG. 13 depicts the molecular structure of alpha-pinene.
Figure 14:
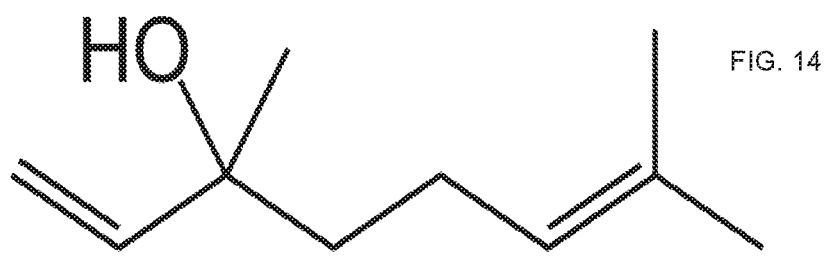
FIG. 14 depicts the molecular structure of linalool.
Figure 15:
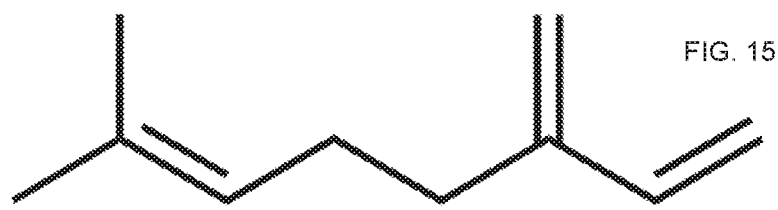
FIG. 15 depicts the molecular structure of myrcene.
Figure 16:
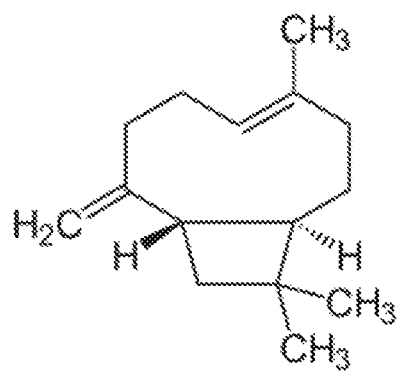
FIG. 16 depicts the molecular structure of beta-caryophyllene.
Figure 17:
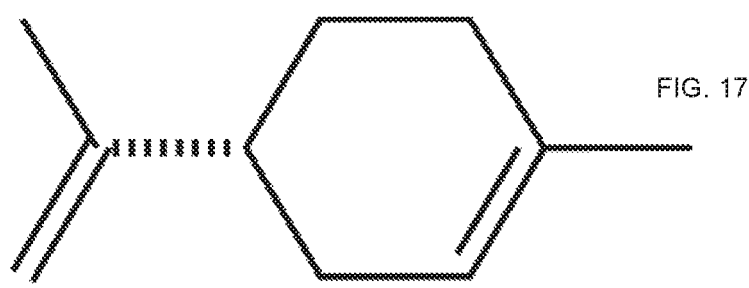
FIG. 17 depicts the molecular structure of limonene.

If the cannabis extract was solvent based then the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation step can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. Not all ingredients or steps listed above must be performed. For example, (1) omission of nutrients, surfactants, or food coloring does not constitute a new product and (2) omission of the freezing step does not constitute a new manufacturing process.

Example 3

Cannabis Extraction Using the *Cannabis Sativa* Strain

Starting with cannabis plant material that originates from any and all *cannabis sativa* strains (and any/all subspecies— in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, *yucca* extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. Not all ingredients or steps listed above must be performed. For example, (1) omission of nutrients, surfactants, or food coloring does not constitute a new product and (2) omission of the freezing step does not constitute a new manufacturing process.

Example 4

Cannabis Extraction Using an Established Strain

Starting with cannabis plant material that originates from any and all established strains, for example Sour Diesel strain and any/all sub strains (in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents from be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation step can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, *yucca* extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. Not all ingredients or steps listed above must be performed. For example, (1) omission of nutrients, surfactants, or food coloring does not constitute a new product and (2) omission of the freezing step does not constitute a new manufacturing process.

Example 5

Cannabis Extraction Using Live Plant Material that is not Dried or Cured

Starting with live/not dried cannabis plant material that originates from any and all *cannabis* species (including but not limited to *cannabis sativa, cannabis indica, cannabis ruderalis*—and any/all subspecies and any/all cross breeds thereof—in both male and female varieties) the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. Not all ingredients or steps listed above must be performed. For example, (1) omission of nutrients, surfactants, or food coloring does not constitute a new product and (2) omission of the freezing step does not constitute a new manufacturing process.

Example 6

Cannabis Extraction to Produce Kosher Extracts

Starting with cannabis plant material that originates from any and all *cannabis* species (including but not limited to *cannabis sativa, cannabis indica, cannabis ruderalis*—and any/all subspecies and any/all cross breeds thereof—in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation step can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. Not all ingredients or steps listed above must be performed. For example, (1) omission of nutrients, surfactants, or food coloring does not constitute a new product and (2) omission of the freezing step does not constitute a new manufacturing process.

Example 7

Cannabis Extraction to Produce Halal Extracts

Under Islamic Law, as it pertains to dietary restrictions, anything that is considered "kosher" is also considered halal. Therefore the composition of this formulation will be exactly the same as that of Example 6.

Example 8

Cannabis Extraction to Produce Vegan Extracts

Starting with cannabis plant material that originates from any and all *cannabis* species (including but not limited to *cannabis sativa, cannabis indica, cannabis ruderalis*—and any/all subspecies and any/all cross breeds thereof—in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation step can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients used in this vegan variety will be sourced from non-animal sources. All ingredients may vary in ratio in final product, from 0-100% by weight. Not all ingredients or steps listed above must be performed. For example, (1) omission of nutrients, surfactants, or food coloring does not constitute a new product and (2) omission of the freezing step does not constitute a new manufacturing process.

Example 9

Cannabis Extraction to Produce Gluten-Free Extracts

Starting with cannabis plant material that originates from any and all *cannabis* species (including but not limited to *cannabis sativa, cannabis indica, cannabis ruderalis*—and any/all subspecies and any/all cross breeds thereof—in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation step can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. All ingredients used in this variety will be gluten-free. Not all ingredients or steps listed above must be performed. For example, (1) omission of nutrients, surfactants, or food coloring does not constitute a new product and (2) omission of the freezing step does not constitute a new manufacturing process.

Example 10

Cannabis Extraction that does not Utilize a Decarboxylation Step

Starting with cannabis plant material that originates from any and all *cannabis* species (including but not limited to *cannabis sativa, cannabis indica, cannabis ruderalis*—and any/all subspecies and any/all cross breeds thereof—in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. In this embodiment, the cannabis/cannabis extract will not be decarboxylated. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. Not all ingredients or steps listed above must be performed. For example, (1) omission of nutrients, surfactants, or food coloring does not constitute a new product and (2) omission of the freezing step does not constitute a new manufacturing process.

Example 11

Producing a Highly Potent Cannabis Extract

Starting with cannabis plant material that originates from any and all *cannabis* species (including but not limited to *cannabis sativa, cannabis indica, cannabis ruderalis*—and any/all subspecies and any/all cross breeds thereof—in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. For a high potency version a greater ratio of cannabis extract to the organic medium and other ingredients is used. For example, in this embodiment the ratio of cannabis extract to lipids and other ingredients may be 10:1. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. Not all ingredients or steps listed above must be performed. For example, (1) omission of nutrients, surfactants, or food coloring does not constitute a new product and (2) omission of the freezing step does not constitute a new manufacturing process.

Example 12

Producing a Low Potency Cannabis Extract

Starting with cannabis plant material that originates from any and all *cannabis* species (including but not limited to *cannabis sativa, cannabis indica, cannabis ruderalis*—and any/all subspecies and any/all cross breeds thereof—in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation step can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. For a low potency version a smaller ratio of cannabis extract to the organic medium and other ingredients is used. For example, in this embodiment the ratio of cannabis extract to lipids and other ingredients may be 1:10. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. Not all ingredients or steps listed above must be performed. For example, (1) omission of nutrients, surfactants, or food coloring does not constitute a new product and (2) omission of the freezing step does not constitute a new manufacturing process.

Example 13

Producing a CBD Cannabis Extract

Starting with cannabis plant material that originates from any and all *cannabis* species that have determined and high concentrations of CBD, like "Charlotte's Web" for example (including but not limited to *cannabis sativa, cannabis indica, cannabis ruderalis*—and any/all subspecies and any/all cross breeds thereof—in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents can be from the extract while retaining compounds of pharmaceutical and organoleptic interest. Next, the sample is fully (or partially) decarboxylated (at a variety of temperatures (~90-180° C.), pressures, methods, and durations can vary depending on batch size, desired characteristics of final product, and other factors). This decarboxylation step may be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. Not all ingredients or steps listed above must be performed. For example, (1) omission of nutrients, surfactants, or food coloring does not constitute a new product and (2) omission of the freezing step does not constitute a new manufacturing process.

Example 14

Producing an Extended Release Cannabis Extract

Starting with cannabis plant material that originates from any and all *cannabis* species (including but not limited to *cannabis sativa, cannabis indica, cannabis ruderalis*—and any/all subspecies and any/all cross breeds thereof—in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents cam be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation step can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Nutritional compounds (including but not limited to: alcohols, fats, carbohydrates, and proteins) are optionally added to the mixture. Food coloring may also be added at this point. Optionally, a FAAH inhibitor can be added to the mixture—drastically limiting the degradation of cannabinoids in the mammalian endocannabinoid system and resulting in prolonged psychoactive and medicinal effects. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. Not all ingredients or steps listed above must be performed. For example, (1) omission of nutrients, surfactants, or food coloring does not constitute a new product and (2) omission of the freezing step does not constitute a new manufacturing process.

Example 15

Producing an Allergen Free Cannabis Extract

Starting with cannabis plant material that originates from any and all *cannabis* species (including but not limited to *cannabis sativa, cannabis indica, cannabis ruderalis*—and any/all subspecies and any/all cross breeds thereof—in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation step can be performed in an airtight container in order to prevent and limit the escape and degradation of vaporized medically viable compounds including but not limited to terpenes and cannabinoids. Next, an allergen-free organic medium (including but not limited to: lipids, alcohols, etc.) and allergen-free surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Optionally, allergen-free nutritional compounds (including but not limited to: alcohols, fats, carbohydrates, and proteins) are added to the mixture. Food coloring may also be added at this point. The mixture is then optionally frozen. Further iterations of heating and freezing may be utilized. The mixture is then filtered and used to fill gelatin capsules. The capsules are then stored.

All ingredients may vary in ratio in final product, from 0-100% by weight. All ingredients will be sourced from allergen-free sources. Not all ingredients or steps listed above must be performed. For example, (1) omission of nutrients, surfactants, or food coloring does not constitute a new product and (2) omission of the freezing step does not constitute a new manufacturing process.

Example 16

Producing a Low Sodium or Sodium Free Cannabis Extract

Starting with cannabis plant material that originates from any and all *cannabis* species (including but not limited to *cannabis sativa, cannabis indica, cannabis ruderalis*—and any/all subspecies and any/all cross breeds thereof—in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation step can be performed in an airtight container to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/golden in color. It is then filtered and used to fill gelatin capsules. The capsules are then stored.

All ingredients may vary in ratio in final product, from 0-100% by weight. All ingredients will contain very little to no sodium. Not all ingredients or steps listed above must be performed. For example, (1) omission of nutrients, surfactants, or food coloring does not constitute a new product and (2) omission of the freezing step does not constitute a new manufacturing process.

Example 17

Examples of Other Cannabis Extracts

Starting with cannabis plant material that originates from any and all *cannabis* species (including but not limited to *cannabis sativa, cannabis indica, cannabis ruderalis*—and any/all subspecies and any/all cross breeds thereof—in both male and female varieties), the sample is dried and cured (proper drying and storage protocol ensures maximal terpene content), then the medically viable compounds (primarily cannabinoids and terpenes) are extracted from the plant material using a variety of extraction methods (including but not limited to: cold water extraction and dry sift (hash), CO2, hydrocarbons (including but not limited to: butane, propane, hexane), alcohol (including but not limited to: ethanol, iso-propyl, methanol), and rosin tech (heat extraction)) or alternatively, no extraction is performed.

If the cannabis extract was solvent based then the residual solvents can be purged from the extract while retaining compounds of pharmaceutical and organoleptic interest (described in FIG. 3). Next, the sample is fully (or partially) decarboxylated (at a variety of temperatures (~90-180° C.), pressures, methods, and durations can vary depending on batch size, desired characteristics of final product, and other factors). This decarboxylation step can be performed in an airtight container in order to prevent and limit the escape and degradation of vaporized medically viable compounds including but not limited to terpenes and cannabinoids. Next, an organic medium (including but not limited to: lipids, alcohols, etc.) and surfactant(s) (including but not limited to: soy lecithin, egg yolk, yucca extract) are added to the decarboxylated extract (or decarboxylated plant material) the mixture is then optionally heated (temperatures (~90-180° C.) and durations can vary depending on batch size, desired characteristics of final product, and other factors). Varying the temperatures, pressures, methods, and durations of heat exposure can greatly influence the medical characteristics of the final product. Nutritional compounds (including but not limited to: alcohols, fats, carbohydrates, and proteins) are optionally added to the mixture. Food coloring may also be added at this point. The mixture is then optionally frozen. Further iterations of heating and freezing may be utilized. The mixture should be yellow/light brown/ golden in color. It is then filtered and used to fill gelatin capsules. The capsules are then stored.

All ingredients may vary in ratio in final product, from 0-100% by weight. ALL ingredients will contain very little to no sodium. Not all ingredients or steps listed above must be performed. For example, (1) omission of nutrients, surfactants, or food coloring does not constitute a new product and (2) omission of the freezing step does not constitute a new manufacturing process.

Example 18

Cooks were Performed Using the Following Naming Convention: "Cook 1" and "Cook 3"

"Cook 1" used 3.00 grams of cannabis extract with the strain name Afghan Skunk (Washington Liquor and Cannabis Control Board Lot #6034347010022992). This cannabis extract was made using a hydrocarbon extraction of cannabis plant material. The Device chamber was flushed with nitrogen prior to the cook. The Device chamber and cannabis extract were then heated to 250° F. for a duration of 1.5 hours. The valve leading from The Device chamber to the size exclusion filter was left open throughout the cook. The coil proceeding the size exclusion filter was cooled for the duration of the cook using an ice bath. After allowing The Device chamber to cool to room temperature (approximately 45 minutes), 60 mL of iso-propyl alcohol was then used to flush the coil to recapture any condensed terpenes, this same aliquot of isopropyl alcohol was then used to dissolve the extract after the cook had completed.

"Cook 3" used 3.00 grams of cannabis extract with the strain name Afghan Skunk (Washington Liquor and Cannabis Control Board Lot #6034347010022992). This cannabis extract was made using a hydrocarbon extraction of cannabis plant material. For the duration of this cook the vessel was exposed to ambient conditions (matching prior art preparations). The vessel and cannabis extract were then heated to 250 F for a duration of 1.5 hours. After allowing the vessel to cool to room temperature (approximately 45 minutes), 60 mL of iso-propyl alcohol was then used to dissolve the extract after the cook had completed.

Figure 24:
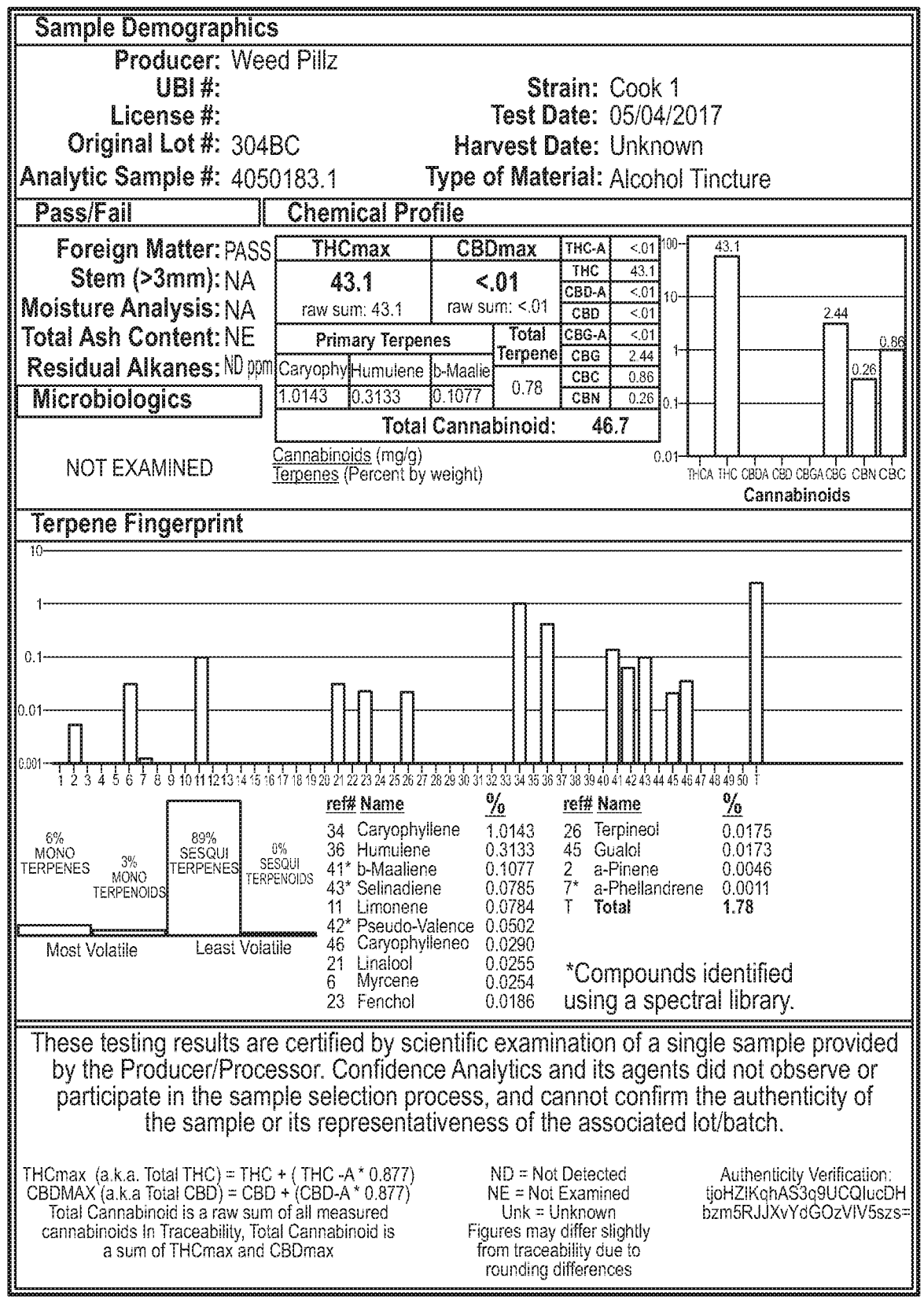
FIG. 24 depicts results from a cannabis extraction experiment in which the extract was heated to 250° F. for a duration of 1.5 hours.
Figure 25:
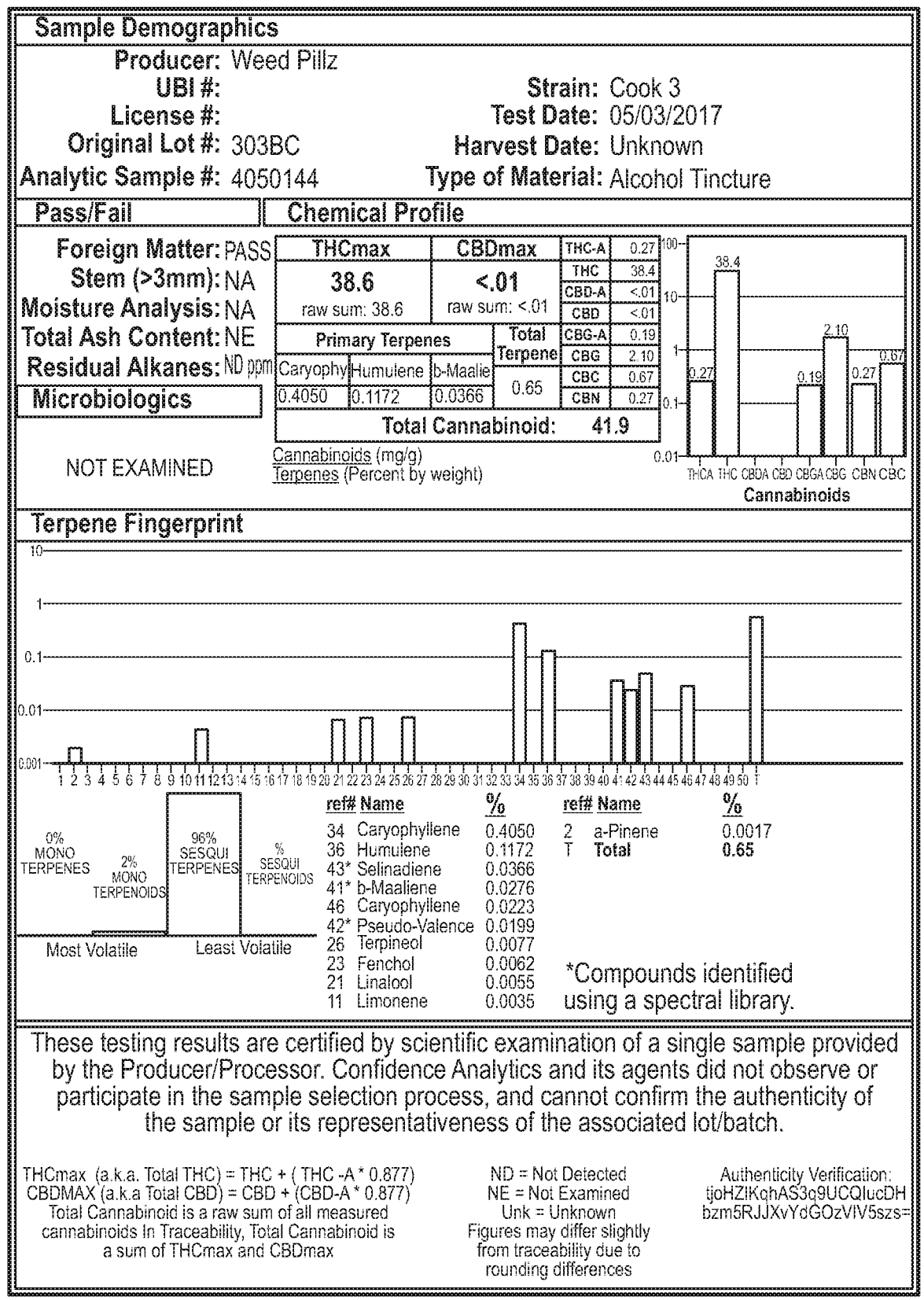
FIG. 25 depicts results from a cannabis extraction experiment in which the extract was exposed to ambient temperatures throughout the duration of the extraction process.

Included is the data corresponding to these two cooks. The data for "Cook 1" is shown in FIG. 24. The data for "Cook 3" is shown in FIG. 25. As shown by this data, "Cook 1" contained 2.74×the terpene content found in "Cook 3" while containing relatively the same cannabinoid content. Furthermore "Cook 1" contained virtually no THC-A while "Cook 3" contained 0.27 mg/g of THC-A. This shows that the decarboxylation process occurred to completion in "Cook 1", the same could not be said for Cook 3 "Cook 1" had a greater terpene diversity than "Cook 3". In "Cook 1", 6% of the terpenes quantified were monoterpenes, 3% were monoterpenoids, and 89% sesquiterpenes. In "Cook 3", 0% of the terpenes quantified were monoterpenes, 2% were monoterpenoids, 96% were sesquiterpenes. It should be noted that when ranked by volatility, monoterpenes are the most volatile followed by monoterpenoids, then sesquiterpenes, and lastly sesquiterpenoids.

The data indicates that using an N2 flush, a cooling coil, and a size exclusion filter, is more effective at retaining terpenes and progressing the decarboxylation process. "Cook 1" progressed the decarboxylation of other cannabinoids in addition to THC-A, such as CBG-A. Increasing the diversity of active cannabinoids and terpenes further enforces the entourage effect discussed at length in this disclosure.

The examples can be combined. For example: (1) a gluten free preparation that originates from a *cannabis indica* strain that is kosher and extremely potent (2) allergen-free preparation that originates from a *cannabis sativa* strain that is halal and sodium free and low potency (3) a CBD rich preparation that originates from live plant material and is extended release, vegan, and non-decarboxylated—using an established strain.

A method of cannabis extraction, comprising the steps of: (i) adding an amount of at least one species of *cannabis* plant or an amount of an extract of at least one species of *cannabis* plant to a reaction chamber; (ii) removing byproducts from the reaction chamber that are produced from extracting cannabis; and (iii) retaining compounds within the chamber derived from cannabis, wherein the reaction chamber comprises a filter comprising pores that allow for removal from the reaction chamber of the byproducts from the cannabis extraction process and prevent removal or escape from the chamber of the compounds derived from the at least one cannabis plant or extract of at least one species of *cannabis* plant.

In some embodiments the at least one cannabis plant is at least one from the group consisting of *Cannabis sativa, Cannabis indica,* and *Cannabis ruderalis*. In some embodiments, the reaction chamber is an airtight chamber. In some embodiments, extracting cannabis comprises a solvent based extraction. In some embodiments, the solvent is at least one from the group consisting of iso-propyl, methanol, n-propyl alcohol, propane, butane, iso-butane, methanol, and ethanol. In some embodiments, extracting cannabis does not use a solvent. In some embodiments, the non-solvent extraction is at least one from the group consisting of a heat extraction, an unheated extraction, a cold water extraction, a $CO_2$ extraction, and a rosin tech extraction. In some embodiments, the method further comprises a decarboxylation step wherein the extracts or the cannabis plant material are decarboxylated. In some embodiments, the method further comprises removing $CO_2$ from the reaction chamber after decarboxylating the extracts or cannabis plant material. In some embodiments, the $CO_2$ is removed through the filter. In some embodiments, the decarboxylation reaction occurs in the presence of an inert gas. In some embodiments the reaction chamber will be treated with an inert gas before prior to the decarboxylation step. In some embodiments, the inert gas is at least one from the group consisting of helium, neon, argon krypton, xenon, and radon. In some embodiments, the decarboxylation step further comprises using a targeted enzyme or cofactor.

In some embodiments, the decarboxylation step further comprises $H_2O$ as a catalyst. In some embodiments, the reaction chamber further comprises a magnetic stir bar. In some embodiments, the cannabis extract that originates from live cannabis material. In some embodiments, the cannabis extract originates from dried/cured cannabis plant material. In some embodiments, the compounds within the chamber derived from cannabis comprise at least one cannabinoid and at least one terpene. In some embodiments, the compounds within the chamber derived from cannabis comprise cannabinoids, terpenes/terpenoids, amino acids, nitrogenous compounds, simple alcohols, aldehydes, ketones, esters, lactones, and acids, fatty acids, steroids, non-cannabinoid phenols, pigments, flavonoids, vitamins, proteins, enzymes, glycoproteins, and hydrocarbons. In some embodiments, the compounds within the chamber derived from cannabis in step (iv) comprise the at least about 545 distinct compounds in cannabis.

In some embodiments, the method of cannabis extraction comprises using a surfactant. In some embodiments the method of cannabis extraction comprises using an emulsifier. In some embodiments, the method of cannabis extraction uses any one or more species of *cannabis*. In some embodiments, the method of cannabis extraction comprises using any one one or more subspecies of *cannabis* plant. In some embodiments, the method of cannabis extraction comprises using any one or more strains of cannabis plant. In some embodiments, the method of cannabis extraction comprises using a cannabis plant derived from a female source. In some embodiments, the method of cannabis extraction comprises using a cannabis plant derived from a male source.

In some embodiments, an apparatus for the extraction of cannabis is provided comprising: (i) an airtight container comprising: (ii) an inner surface; (iii) an outer surface; (iv) a reaction chamber; and (iv) a size exclusion filter, wherein the size exclusion filter comprises pores of sufficient size to allow byproducts of an extraction process and a decarboxylation process to pass through the filter but prevents compounds derived from cannabis from passing through the filter. In some embodiments, the pores are from about 0.01 $Å^2$ to 100 $Å^2$.

In some embodiments, the reaction chamber comprises a stir bar. In some embodiments, the reaction chamber is temperature controlled and pressure controlled. In some embodiments, the stir bar is a magnetic stir bar. In some embodiments, the apparatus further comprises a stirring base that rotates the stir bar. In some embodiments, the magnetic stir bar is coated with a non-stick coating. In some embodiments, the inner surface of the apparatus comprises a non-stick coating. In some embodiments, the non-stick coating is silicone. In some embodiments, the apparatus further comprises a loading door. In some embodiments, the apparatus further comprises a steel rod wherein the steel rod is within the reaction chamber, and wherein the steel rod is attached to the size exclusion filter. In some embodiments, the steel rod passes through the center of the reaction chamber. In some embodiments, the size exclusion filter is configured to move up and down on the steel rod within the reaction chamber. In some embodiments, the reaction chamber further comprises at least one valve. In some embodiments the at least one valve comprises two valves.

In some embodiments a cannabis extraction method is provided comprising using any of the apparatuses disclosed herein comprising the steps of: (i) adding at least one species of cannibas plant or extract of at least one species of *cannabis* plant to a reaction chamber; (ii) producing cannabis extracts through extracting cannabis from the at least one plant or extract of at least one species of *cannabis* plant in the reaction chamber; (iii) removing byproducts from the reaction chamber that are produced from extracting cannabis; and (iv) retaining compounds within the chamber derived from cannabis, wherein the reaction chamber comprises a filter, and wherein pores in the filter allow for removal from the reaction chamber of the byproducts from the cannabis extraction process and prevent removal or escape from the chamber of the compounds derived from cannabis.

In some embodiments, an isolated mixture of compounds is provided, comprising at least one terpene compound derived from cannabis and at least one cannabinoid compound derived from cannabis. In some embodiments the mixture of compounds comprises at least 5 terpene compounds derived from cannabis. In some embodiments the mixture of compounds comprises at least 10 terpene compounds derived from cannabis. In some embodiments the mixture of compounds comprises at least 15 terpene compounds derived from cannabis. In some embodiments the mixture of compounds comprises at least 20 terpene compounds derived from cannabis. In some embodiments, the mixture of compounds is 24 terpene compounds derived from cannabis. In some embodiments, the 24 terpene compounds derived from cannabis comprise: α-Pinene, Camphene, β-Pinene, β-Myrcene, 3-Carene, α-Terphinene, D-Limonene, p-Cymene, Eucalyptol, cis-β-Ocimene, γ-Terpinen, Terpinolene, Linalool, trans-β-Ocimene, Fenchol, Isopulegol, Geraniol, β-Caryophyllene, α-Humulene, cis-Nerolidol, trans-Nerolidol, Guaiol, Caryophyllene Oxide, and α-Bisabolol.

In some embodiments the percent mass of each terpene compound is between 0.0001% and 010%. In some embodiments, the percent mass of each terpene compound is between 0.0005% and 0.07%. In some embodiments, the percent mass of each compound is between 0.001% and 0.05%.

In some embodiments the mixture of compounds comprises at least 3 cannabinoid compounds derived from cannabis. In some embodiments, the mixture of compounds comprises 7 cannabinoid compounds derived from cannabis. In some embodiments, the 7 cannabinoid compounds derived from cannabis comprise: THC-A, CBL-A, $Δ^9$-THC, CBN, CBC, CBG, and THCV. In some embodiments, the mg/ml of each cannabinoid is between 0.01 mg/ml and 1,000 mg/ml. In some embodiments, the mg/ml of each cannabinoid is between 0.1 mg/ml and 25 mg/ml.

In some embodiments, the mixture of compounds is in a capsule. In some embodiments, the capsule is a gelatin capsule. In some embodiments the capsule comprises a pharmaceutical formulation.

In some embodiments a method of cannabis extraction is provided wherein the cannabis plant that is added is *Cannabis sativa*. In some embodiments, the cannabis plant that is added *Cannabis indica*. In some embodiments, the cannabis plant that is added is *Cannabis ruderalis*.

In some embodiments, a method of treatment is provided comprising: administering a pharmaceutically acceptable amount of the mixture to a patient in need thereof.

In some embodiments, administering the mixture to the patient results in the patient experiencing the entourage effect. In some embodiments, the treatment is for any one or more of the following: nausea and vomiting, wasting syndrome (AIDS), lack of appetite (exhibited in cancer and AIDs patients as well as patients suffering from anorexia nervosa), multiple sclerosis, spinal cord trauma, epilepsy, pain, arthritis (and other musculoskeletal disorders), movement disorders, glaucoma, asthma, hypertension, psychiatric disorders, Alzheimer's and dementia, general inflammation, gastrointestinal disorders.

In some embodiments, the compounds within the chamber derived from cannabis comprise cannabinoids, nitrogenous compounds, amino acids, proteins, enzymes, glycoproteins, hydrocarbons, simple alcohols, aldehydes, ketones and acids, fatty acids, simple esters and lactones, steroids, terpenes, non-cannabinoid phenols, flavonoids, vitamins, and pigments.

In some embodiments, an isolated mixture of compounds derived from cannabis is provided comprising cannabinoids, nitrogenous compounds, amino acids, proteins, enzymes, glycoproteins, hydrocarbons, simple alcohols, aldehydes, ketones and acids, fatty acids, simple esters and lactones, steroids, terpenes, non-cannabinoid phenols, flavonoids, vitamins, and pigments. In some embodiments, the mixture of compounds is contained within a capsule. In some embodiments, the capsule is a gelatin capsule. In some embodiments, the capsule comprises a pharmaceutical formulation.

In some embodiments, a method of treatment is provided comprising: administering a pharmaceutically acceptable amount of the mixture to a patient in need thereof. In some embodiments, the treatment is for the purpose of treating any one or more of the following: nausea and vomiting, wasting syndrome (AIDS), lack of appetite (exhibited in cancer and AIDs patients as well as patients suffering from anorexia nervosa), multiple sclerosis, spinal cord trauma, epilepsy, pain, arthritis (and other musculoskeletal disorders), movement disorders, glaucoma, asthma, hypertension, psychiatric disorders, Alzheimer's and dementia, general inflammation and gastrointestinal disorders.

In some embodiments, a method is provided comprising the steps of: (i) adding cannabis or cannabis extract to a reaction chamber; (ii) removing byproducts from the reaction chamber produced from processing cannabis; and (iii) retaining compounds within the chamber derived from cannabis, wherein the reaction chamber comprises a filter comprising pores that allow for removal from the reaction chamber of the byproducts produced from processing cannabis and prevent removal or escape from the chamber of the compounds derived from the cannabis or cannabis extract.

The foregoing written specification is considered to be sufficient to enable one skilled in the art to practice the present embodiments. The foregoing description details certain preferred embodiments and describes the best mode contemplated by the inventors. It will be appreciated, however, that no matter how detailed the foregoing may appear in text, the present embodiments may be practiced in many ways and the present embodiments should be construed in accordance with the appended claims and any equivalents thereof.

What is claimed is:

1. A method of preparing a decarboxylated cannabis extract, comprising:
    applying an extraction process to cannabis to yield a cannabis extract:
    adding the cannabis extract to a reaction chamber;
    treating the reaction chamber with an inert gas selected from the group consisting of nitrogen, helium, neon and argon;
    in the presence of the inert gas, initiating a decarboxylation process at a temperature of about 90° C. to about 180° C. on the cannabis extract to result in a decarboxylated cannabis extract and byproducts produced from the decarboxylation process;
    condensing, within the reaction chamber by freezing the decarboxylated cannabis extract, and removing byproducts from the reaction chamber;
    retaining, within the reaction chamber, the decarboxylated cannabis extract; and
    removing, from the reaction chamber, the decarboxylated cannabis extract.

2. The method of claim 1, wherein the cannabis is selected from the group consisting of *Cannabis sativa, Cannabis indica, Cannabis ruderalis*, hybrids thereof, and combinations thereof.

3. The method of claim 1, wherein the reaction chamber is an airtight chamber.

4. The method of claim 1, wherein the extraction process is a solvent-based extraction.

5. The method of claim 4, wherein the solvent is selected from the group consisting of an alcohol solvent, a lipid solvent, a hydrocarbon solvent, a $CO_2$ solvent, a water-based solvent, and combinations thereof.

6. The method of claim 1, wherein the extraction process is an extraction without a solvent.

7. The method of claim 6, wherein the extraction is selected from the group consisting of heat extraction, unheated extraction, rosin tech extraction, and combinations thereof.

8. The method of claim 1, wherein the byproducts comprise $CO_2$.

9. The method of claim 8, wherein the $CO_2$ is removed through a filter comprising pores that allow for removal from the reaction chamber of the $CO_2$ and prevents removal or escape from the chamber of the decarboxylated cannabis extract.

10. The method of claim 1, wherein the decarboxylation process comprises using a targeted enzyme or cofactor.

11. The method of claim 1, wherein the decarboxylation process comprises application of $H_2O$ as a catalyst.

12. The method of claim 1, wherein the reaction chamber further comprises a stirrer.

13. The method of claim 1, wherein the cannabis is not dried.

14. The method of claim 1, wherein the cannabis is dried.

15. The method of claim 1, wherein the decarboxylated cannabis extract comprises at least one cannabinoid and at least one terpene.

16. The method of claim 1, wherein the decarboxylated cannabis extract comprises cannabinoids, terpenes/terpenoids, amino acids, nitrogenous compounds, simple alcohols, aldehydes, ketones, esters, lactones, and acids, fatty acids, steroids, non-cannabinoid phenols, pigments, flavonoids, vitamins, proteins, enzymes, glycoproteins, and hydrocarbons.

17. The method of claim 9, wherein the pores are from about 29 $Å^2$ to about 31 $Å^2$.

18. The method of claim 1, wherein the reaction chamber is adjusted to the freezing temperatures of the decarboxylated cannabis extract using an ice bath.

19. The method of claim 1, wherein the decarboxylated cannabis extract partially comprises non-decarboxylated cannabis extract.

* * * * *